US012797128B2

(12) United States Patent
Strong et al.

(10) Patent No.: US 12,797,128 B2
(45) Date of Patent: Nov. 17, 2026

(54) CATHETER SYSTEM FOR MAKING A SURGICAL CUT IN THE PERICARDIUM

(71) Applicant: Heart Failure Solutions, Inc., Shoreview, MN (US)

(72) Inventors: Mark Henry Strong, Shoreview, MN (US); Alexandra Dean Bursey, Hopkins, MN (US)

(73) Assignee: Heart Failure Solutions, Inc., Shoreview, MN (US)

( * ) Notice: Subject to any disclaimer, the term of this patent is extended or adjusted under 35 U.S.C. 154(b) by 0 days.

(21) Appl. No.: 19/323,513

(22) Filed: Sep. 9, 2025

(65) Prior Publication Data

US 2026/0130710 A1 May 14, 2026

Related U.S. Application Data

(60) Provisional application No. 63/719,359, filed on Nov. 12, 2024.

(51) Int. Cl.
*A61B 18/14* (2006.01)
*A61B 17/32* (2006.01)
(Continued)

(52) U.S. Cl.
CPC .. *A61B 18/1492* (2013.01); *A61B 17/320016* (2013.01); *A61B 17/3211* (2013.01);
(Continued)

(58) Field of Classification Search
CPC . A61B 18/14; A61B 18/1492; A61B 18/1402; A61B 18/148; A61B 18/1482;
(Continued)

(56) References Cited

U.S. PATENT DOCUMENTS 8,425,507 B2 * 4/2013 Pellegrino ............... A61F 7/007 606/41
8,986,278 B2 * 3/2015 Fung .................. A61B 17/3478 604/500
(Continued)

FOREIGN PATENT DOCUMENTS

WO 2023/229938 11/2023
WO 2023/235263 12/2023
WO 2024/129360 6/2024

OTHER PUBLICATIONS

International Search Report and Written Opinion for International PCT Patent Application No. PCT/US25/55132 mailed Feb. 23, 2026 (15 pages).

*Primary Examiner* — Thomas A Giuliani
(74) *Attorney, Agent, or Firm* — Fox Rothschild LLP

(57) ABSTRACT

This document describes a catheter system for creating an opening in a pericardium. The catheter system includes a sheath defining a sheath lumen that includes a distal opening and a catheter sized to slidably fit within the sheath lumen so that the catheter extends through an entire length of the sheath lumen with a distal portion of the catheter extending beyond the distal opening of the sheath lumen and into a space underneath a pericardium of a patient. Additionally, the catheter system includes a blade movably mounted to the distal portion of the catheter to move from a retracted position to an actuated position. The blade remains fully within an outer housing of the catheter when the blade is in the retracted position. The blade extends outward from the catheter when the blade is in the actuated position so that the blade cuts the pericardium as the catheter withdraws.

26 Claims, 13 Drawing Sheets

(51) Int. Cl.

| | |
|---|---|
| ***A61B 17/3211*** | (2006.01) |
| ***A61M 5/00*** | (2006.01) |
| ***A61M 25/01*** | (2006.01) |
| ***A61M 25/09*** | (2006.01) |
| ***A61M 29/02*** | (2006.01) |
| *A61B 17/00* | (2006.01) |
| *A61B 18/00* | (2006.01) |

(52) U.S. Cl.

CPC ........ *A61M 5/007* (2013.01); *A61M 25/0147* (2013.01); *A61M 25/09* (2013.01); *A61M 29/02* (2013.01); *A61B 2017/00039* (2013.01); *A61B 2017/00084* (2013.01); *A61B 2017/00243* (2013.01); *A61B 2017/00323* (2013.01); *A61B 2017/00367* (2013.01); *A61B 2017/32113* (2013.01); *A61B 2018/00351* (2013.01); *A61B 2018/00601* (2013.01); *A61B 2018/00642* (2013.01); *A61B 2018/00791* (2013.01); *A61B 2018/00839* (2013.01); *A61B 2018/1412* (2013.01)

(58) Field of Classification Search

CPC ........ A61B 18/1487; A61B 17/320016; A61B 17/3211; A61B 2017/00243; A61B 2017/00323; A61B 2017/00367; A61B 2017/32113; A61B 2018/1472; A61B 2018/1475; A61B 2018/00607; A61B 2018/00952; A61B 2018/00351; A61B 2018/00601; A61B 2018/00642; A61B 2018/00791; A61B 2018/00839; A61B 2018/1412; A61B 2018/00005; A61B 2018/00011; A61B 2018/00029; A61B 2018/00202; A61B 2018/00363; A61B 2018/00434

USPC ...... 606/37, 39, 41, 45, 46; 607/98, 99, 101, 607/102, 104, 105, 113, 115, 116, 119, 607/122, 129

See application file for complete search history.

(56) References Cited

U.S. PATENT DOCUMENTS

| | | | | |
|---|---|---|---|---|
| 2006/0184188 | A1* | 8/2006 | Li ...................... | A61B 17/1642 606/180 |
| 2009/0005845 | A1* | 1/2009 | David .................. | A61N 1/0558 607/122 |
| 2010/0036381 | A1* | 2/2010 | Vanleeuwen ...... | A61B 17/8805 606/93 |
| 2011/0098761 | A1* | 4/2011 | Wittenberger ....... | A61B 5/6853 600/301 |
| 2013/0046305 | A1* | 2/2013 | Davies ............... | A61B 18/1492 606/45 |
| 2015/0265304 | A1* | 9/2015 | Feldman .............. | A61B 17/295 606/170 |
| 2016/0015410 | A1* | 1/2016 | Asirvatham ....... | A61B 17/3201 606/49 |
| 2017/0258521 | A1* | 9/2017 | Asirvatham ........... | A61B 8/488 |
| 2019/0111238 | A1* | 4/2019 | Schultz ................ | A61B 5/6869 |
| 2022/0183714 | A1* | 6/2022 | Podmore ........ | A61B 17/320725 |
| 2022/0354526 | A1* | 11/2022 | Mirza ............ | A61B 17/320036 |

* cited by examiner

CATHETER SYSTEM FOR MAKING A SURGICAL CUT IN THE PERICARDIUM

CROSS-REFERENCE TO RELATED APPLICATIONS

This application claims the benefit of U.S. Provisional Application. No. 63/719,359, filed on Nov. 12, 2024 and entitled "Catheter System for Making a Surgical Cut in the Pericardium," the entirety of which is hereby incorporated by reference.

TECHNICAL FIELD

This document relates to systems and methods for performing a pericardiotomy, for example by accessing a space between the pericardium and the myocardium.

BACKGROUND

A pericardiotomy is a surgical procedure involving an incision in the pericardium, the membrane surrounding the heart. One reason to perform a pericardiotomy is to drain excess fluid from the pericardial sac. For example, a clinician can perform a pericardiotomy to treat pericardial effusion, a condition where fluid accumulates around the heart, potentially leading to life-threatening complications such as cardiac tamponade that compromise an ability of the heart to pump effectively. A pericardiotomy can relieve this excess pressure, allowing the heart to function properly. It is also used for diagnostic purposes, allowing doctors to examine the pericardial space or take samples for further testing.

Clinicians often perform pericardiotomies using invasive surgical methods. For example, the patient is typically placed under general anesthesia and the surgeon makes an incision in the chest to open the chest cavity, exposing the heart. This is commonly referred to as "open heart surgery." Once the chest cavity is open, the clinician makes an incision in the pericardium to drain the excess fluid. Because these invasive procedures involve major surgical cuts, patients often need to recover for significant amounts of time after the procedure.

SUMMARY

This document describes devices, systems, and methods for minimally invasive access to the pericardium for purposes of performing a pericardiotomy to treat cardiac diseases and conditions. For example, this document describes catheter devices, systems, and methods for minimally invasive catheter access to a space underneath a pericardium of the patient so that the catheter can make a cut in the pericardium without a need for a major surgical incision in the patient's chest to access the heart. The space underneath the pericardium can, in some embodiments, represent a space between the fibrous pericardium and the serous pericardium sometimes referred to as the "pericardial cavity." These devices, systems, and methods can also provide direct visualization of the catheter during the procedure to guide the physician in making the cut. In some cases, these devices, systems, and methods involve sensing a proximity of a phrenic nerve in the patient's heart so that the clinician can avoid the phrenic nerve in making the cut. The devices, systems, and methods described herein may be used to treat a variety of disorders of the heart including heart failure (HF), heart failure with preserved ejection fraction (HFpEF), heart failure with reduced ejection fraction (HFrEF), and cardiomyopathy.

Some embodiments described herein include an improved instrumentation configured to provide rapid access to the mediastinum and the heart through a small opening in the patient's skin in a manner that provides a clinician an ability to perform a pericardiotomy without using major surgical incisions for access (e.g., open heart surgery). Some embodiments involve techniques for determining a proximity of the phrenic nerve prior to performing the pericardiotomy so that the clinician does not sever or otherwise damage the phrenic nerve during the procedure.

In particular examples described herein, a system can include a sheath handle from which a sheath extends distally, the sheath defining a sheath lumen that is sized to receive one or more objects including a dilator for enlarging a space underneath the pericardium. For example, the dilator can be sized to fit within the sheath lumen so that a distal portion of the dilator extends distally beyond a distal opening of the sheath. A user can grasp the sheath handle and/or a dilator handle of the dilator to simultaneously advance the catheter and the dilator into a small opening in the patient's skin over a guidewire. When the dilator and the sheath simultaneously advance over the guidewire, the distal portion of the dilator can enter a space underneath the pericardium (e.g., a space between the fibrous pericardium and the serous pericardium) to enlarge the space and a distal tip of the sheath can enter the space proximal to the distal portion of the dilator. When the dilator and the sheath are simultaneously advanced into the space underneath the pericardium, the user can remove the guidewire and the dilator through the sheath lumen while the distal tip of the sheath remains in the space. Subsequently, the user can advance a catheter into the space underneath the pericardium through the sheath lumen.

When the catheter is advanced into the space underneath the pericardium such that a distal portion of the catheter is beyond the distal opening of the sheath, the clinician can perform a pericardiotomy using the catheter. In some embodiments, a cutting instrument including a blade is movably attached to the distal portion of the catheter at a hinge. This cutting instrument can occupy a retracted position and an actuated position, the position of the cutting instrument controllable using an actuator on a catheter handle that is fixedly attached to the catheter. In the retracted position, the cutting instrument can be fully within an outer housing of the catheter so that movement of the catheter does not cause the blade instrument to cut or damage tissue. In the actuated position, the cutting instrument can extend outward from the outer housing of the catheter so that movement of the catheter can cause the blade to cut tissue. This means that, in some embodiments, the user can cause the cutting instrument to transition from the retracted position to the actuated position so the blade is positioned to cut the pericardium. For example, as the clinician withdraws the catheter into the sheath, the movement of the catheter causes the blade to cut the pericardium.

The devices, systems, and methods can provide direct visualization of the catheter, sheath, and dilator during the procedure and provide techniques for determining a proximity of one or more nerves (e.g., the phrenic nerve). For example, contrast agent can be delivered through the lumen of the sheath, a lumen of the dilator, a lumen of the catheter, or any combination thereof. This contrast agent can allow the targeted treatment site to be more visible in medical imaging of the procedure. In some cases, the catheter can include one or more electrodes for delivering stimulation to the targeted treatment site and/or sensing one or more signals at the targeted treatment site. For example, sensed signals can indicate a proximity of the phrenic nerve to the distal portion of the catheter. It can be important to avoid damage to the phrenic nerve in performing the pericardiotomy. The contrast agent can assist in techniques to sense these signals. In some cases, any one or combination of the catheter, sheath, and dilator can include radiopaque markers. These radiopaque markers can be visible in medical imaging such that the clinician can determine a position of one or more of the catheter, sheath, and dilator based on a position of the respective radiopaque marker(s) in the medical imaging.

In one aspect, a catheter system for creating an opening in a pericardium includes a sheath defining a sheath lumen that includes a distal opening and a catheter sized to slidably fit within the sheath lumen so that the catheter extends through an entire length of the sheath lumen with a distal portion of the catheter extending beyond the distal opening of the sheath lumen and into a space underneath a pericardium of a patient. The catheter system also includes a blade movably mounted to the distal portion of the catheter to move from a retracted position to an actuated position, wherein the blade remains fully within an outer housing of the catheter when the blade is in the retracted position. The blade extends outward from the catheter when the blade is in the actuated position so that the blade cuts the pericardium as the catheter withdraws into the sheath lumen. In another aspect, a catheter system for creating an opening in a pericardium includes a sheath defining a sheath lumen that includes a distal opening and a dilator sized to slidably fit within the sheath lumen, a distal portion of the dilator extending beyond the distal opening of the sheath lumen so that when the dilator and the sheath simultaneously advance into the patient along a guidewire, the dilator enlarges a space underneath the pericardium of the patient. The catheter system also includes a catheter sized to slidably fit within the sheath lumen after the dilator is removed from the lumen, a distal portion of the catheter extending beyond the distal opening of the sheath lumen and into the space underneath the pericardium of a patient; and a blade mounted on a distal portion of the catheter for cutting the pericardium as the catheter withdraws into the sheath lumen.

In another aspect, a method of performing a procedure to cut a pericardium includes advancing a sheath and a dilator within a lumen of the sheath simultaneously over a guidewire so that a distal portion of the dilator enters a space underneath a pericardium of a patient, enlarging the space as the dilator advances, a distal tip of the sheath located within the space, withdrawing the dilator and the guidewire through the sheath lumen, leaving the distal tip of the sheath within the space, and advancing a catheter through the sheath lumen of the sheath and into the space underneath the pericardium so that a distal portion of the catheter is beyond the distal tip of the catheter and inside of the space. The method also includes transitioning a blade movably mounted on the distal portion of the catheter from a retracted position to an actuated position, the blade in the actuated position extending outward from the catheter; and withdrawing the catheter into the sheath lumen so that the blade cuts the pericardium as the catheter moves relative to the sheath.

Particular embodiments of the subject matter described in this document can be implemented to realize one or more of the following advantages. First, the systems and methods described herein can include specialized techniques and instruments that achieve rapid and minimally invasive access to a space underneath the pericardium (e.g., a space between the fibrous pericardium and the serous pericardium) for the purpose of performing a pericardiotomy. This minimally invasive access can allow a clinician to complete the pericardiotomy without needing to make a major incision in the patient's chest to open the chest cavity and expose the heart.

Second, the systems and methods described herein can advantageously provide techniques for the clinician to safely perform a pericardiotomy while the heart is not visible to the human eye. For example, the clinician can perform the pericardiotomy under direct visualization using one or more medical imaging systems. The catheter system can deliver contrast agent to the targeted treatments site in order to make the patient's anatomy (e.g., the heart and the pericardium) more visible in the medical imaging. Additionally, or alternatively, the catheter can include electrodes for delivering stimulation and/or sensing electrical stimulation. This allows the system to determine a proximity of the phrenic nerve to the blade of the catheter. Based on this information, the clinician can avoid damage to the phrenic nerve in making the pericardiotomy.

The details of one or more embodiments of the invention are set forth in the accompanying drawings and the description herein. Other features, objects, and advantages of the invention will be apparent from the description and drawings, and from the claims.

DETAILED DESCRIPTION

Figure 3:
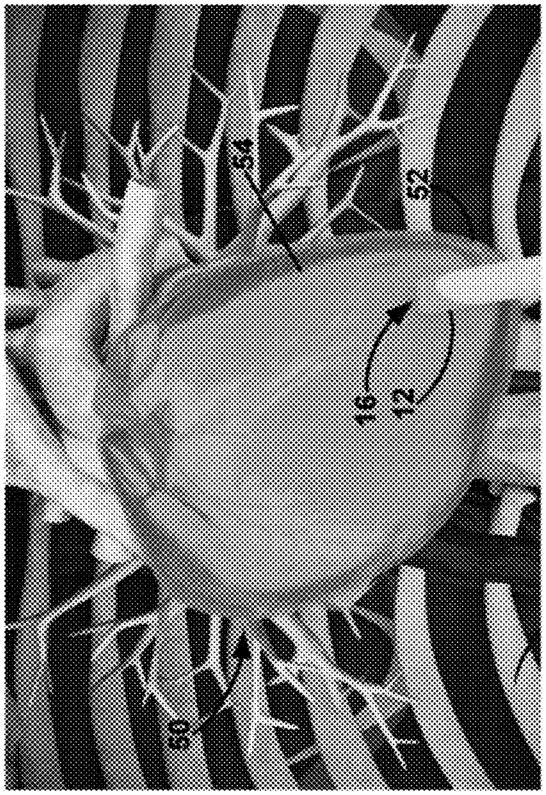
FIG. 3 illustrates the sheath mechanism at the targeted treatment site with the dilator mechanism withdrawn from the targeted treatment site.
Figure 2:
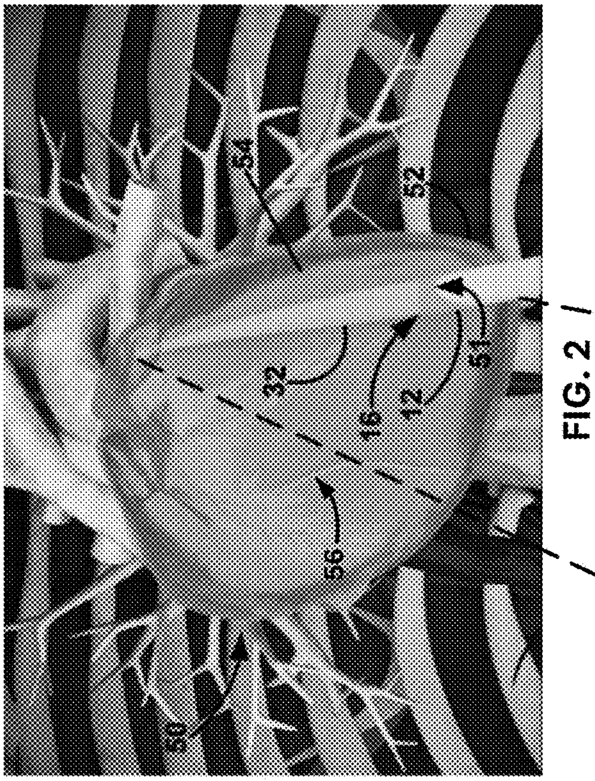
FIG. 2 illustrates the sheath mechanism and the dilator mechanism advanced to a targeted treatment site between the pericardium and the myocardium.
Figure 1:
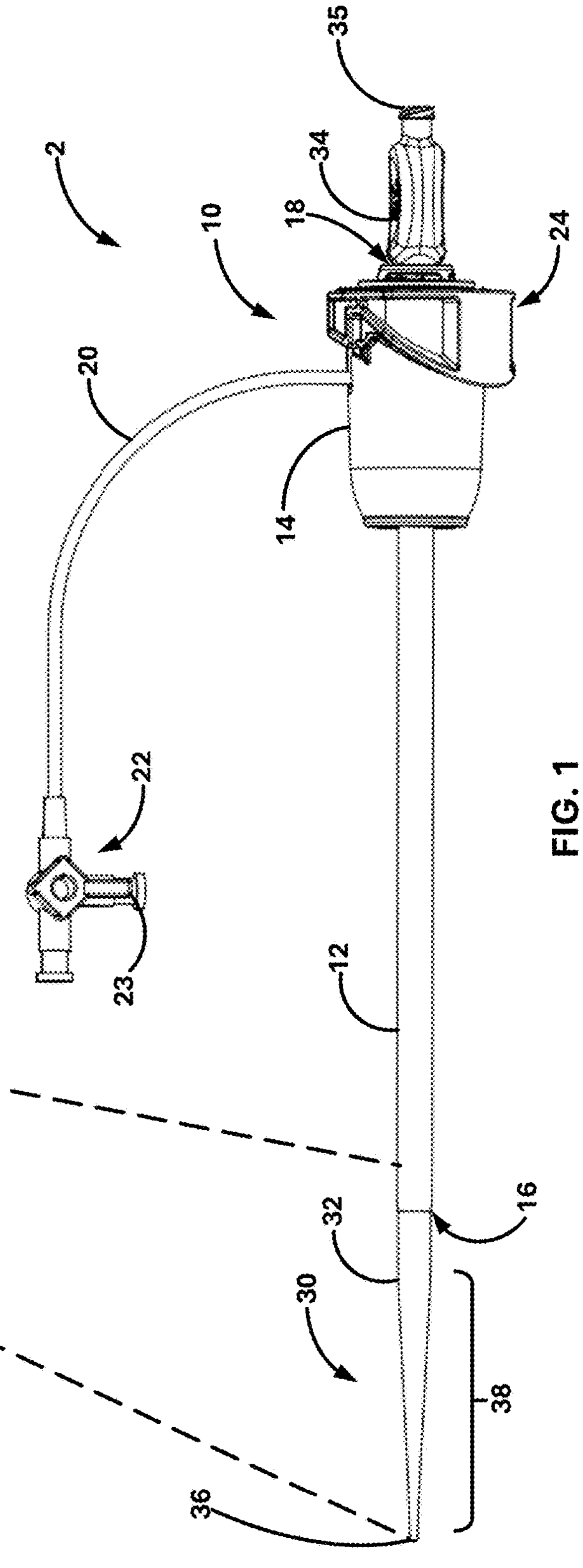
FIG. 1 illustrates a sheath mechanism and a dilator mechanism for preparing a targeted treatment site to perform a surgical procedure.

Referring now to FIGS. 1-3, some embodiments of a system 2 for performing a surgical procedure involving the pericardium to treat one or more cardiac conditions can include a sheath mechanism 10 and a dilator mechanism 30. In some cases, system 2 can be configured to access and engage targeted tissue within a patient. In some examples, this targeted tissue is located within the pericardial sac, such as between the pericardium and the myocardium. The pericardial sac can have several important functions that help to protect and support the heart. For example, the pericardial sac can protect the heart from diseases that spread from nearby tissue. The pericardial sac can also store lubricating fluid between its layers to reduce friction between the heart and surrounding tissues.

In some cases, cardiac conditions can arise involving the pericardium. These conditions include heart failure (HF), heart failure with preserved ejection fraction (HFpEF), heart failure with reduced ejection fraction (HFrEF), and cardiomyopathy, among others. To treat these conditions, it can be beneficial to make one or more surgical cuts in the pericardium. These cuts can release fluid buildup in the pericardial sac or otherwise relieve dangerous restrictions on the ability of the heart to function. One kind of treatment for cardiac conditions involving the pericardium is a pericardiotomy. In some cases, a pericardiotomy involves making an incision in the pericardium without removing the pericardium from the heart. Another kind of treatment for cardiac conditions involving the pericardium is a pericardiectomy. A pericardiectomy is more extensive than a pericardiotomy because a pericardiectomy involves removing part or all of the pericardium from the heart.

It can be beneficial for a procedure involving cuts to the pericardium (e.g., a pericardiotomy and/or a pericardiectomy) to be performed without major surgical incisions to create access to the heart. Highly invasive surgical procedures such as open heart surgery can use these major surgical incisions so that clinicians are able to reach the heart to perform one or more treatments. System 2 may be configured for minimally invasive access to the heart in order to make cuts to the pericardium without using major chest incisions for heart access. For example, system 2 can reach the patient's heart through a small opening in the skin. This minimally invasive access allows the clinician to complete the procedure with less significant trauma to the patient as compared with highly invasive surgeries, thus decreasing the patient's recovery time and decreasing a likelihood of complications relating to surgery.

In some examples, the sheath mechanism 10 includes a sheath body 12 and a sheath handle 14 fixedly connected to the sheath body 12. The sheath body 12 and the sheath handle 14, in some examples, define a sheath lumen that extends through the sheath handle 14 and the sheath body 12 between a distal opening 16 and a proximal opening 18. As depicted in FIG. 1, an outer surface of the sheath body 12 can have a cylindrical shape in some embodiments, a proximal end of the sheath body 12 is fixedly connected to a first end of the sheath handle 14 and a distal end of the sheath body located at the distal opening 16 of the sheath lumen. In some examples, a diameter of sheath body 12 is within a range from 15 French (Fr) to 30 Fr, such as 22 Fr. However, the diameter of sheath body 12 is not limited to this range and can be within another range (e.g., from 5 Fr to 15 Fr, from 10 Fr to 15 Fr, from 30 Fr to 40 Fr). In some examples, a length of sheath mechanism 10 is within a range from 8 centimeters (cm) to 30 cm (e.g., 20 cm). In some embodiments, a length of sheath body 12 is within a range from 6 cm to 20 cm (e.g., 15 cm).

The sheath body 12 can be sized to fit into one or more spaces within tissue of the patient. For example, sheath body 12 can be sized to extend within a passageway from an opening in a patient's skin to the patient's heart. In some examples, the sheath body 12 can extend from an opening in the patient's skin at a midpoint between the xiphoid sternum and a medial border of the inferior rib margin to an opening in the patient's pericardium. This opening in the pericardium, in some examples, can represent an opening in a fibrous pericardium (e.g., an outer layer of the pericardium) so that the sheath body 12 enters a space between the fibrous pericardium and the serous pericardium (e.g., an inner layer of the pericardium).

That is, sheath body 12 can be sized so that the sheath lumen defined by the sheath body 12 can carry one or more objects to the heart of the patient via the opening in the patient's skin. The passageway from the opening to the heart, in some embodiments, extends from the opening to the heart through a mediastinum of the patient. The mediastinum, in some examples, includes soft tissue through which sheath body 12 can pass to reach the heart. Because sheath body 12 is shaped as a narrow tube, sheath body 12 can enter the patient's body through a narrow opening that does not involve the kind of major incision associated with highly invasive procedures such as open heart surgery.

Sheath body 12 can be configured to possess a stiffness sufficient to resist bending when force is applied to sheath body 12. In some embodiments, it can be beneficial for sheath body 12 to resist bending so that the sheath lumen defined by sheath body 12 remains substantially straight. For example, sheath body 12 can slidably receive one or more objects (e.g., the dilator mechanism 30). When the sheath lumen is substantially straight, this makes it easier to slide objects through the sheath lumen as compared with circumstances where the sheath lumen is curved.

In some examples, sheath body 12 is reinforced with a metal braid to provide sufficient stiffness to resist bending. The metal braid can increase an amount of force required to bend sheath body 12 as compared with an amount of force required to bend a sheath body that is not reinforced with a metal braid.

As depicted in FIG. 1, sheath handle 14 is fixedly attached to a proximal end of sheath body 12 so that sheath handle 14 is proximal to sheath body 12. The sheath lumen, in some embodiments, represents a continuous lumen that passes through sheath body 12 and sheath handle 14 between distal opening 16 and proximal opening 18. Sheath handle 14 can have a diameter that is greater than a diameter of sheath body 12. In some examples, the diameter of sheath handle 14 is significantly larger than the diameter of sheath body 12. In some examples, a clinician can grip sheath handle 14 outside of the patient's body while sheath body 12 is inside of the patient. Because the sheath handle 14 can be outside of the patient throughout the entire procedure, the sheath handle 14 can have a larger diameter than the sheath body 12 without a need for a larger opening in the patient to accommodate the larger diameter of the sheath handle 14.

A second end of the sheath handle 14, opposite the first end, can be connected (e.g., at a second end opposite the to a flexible tube 20 that extends from sheath handle 14 to a connector 22. In some examples, flexible tube 20 includes a fluid passageway that is in fluid communication with the sheath lumen defined by sheath body 12 and sheath handle 14. This means that fluid can travel from the connector 22 to the sheath lumen via the flexible tube 20.

In some cases, it is beneficial for flexible tube 20 to be flexible so that, when a clinician maneuvers sheath mechanism 10, these movements are not restricted by stiffness of the flexible tube 20. That is, flexible tube 20 can allow a clinician to freely maneuver sheath mechanism 10 without interference. In some examples, the connector 22 includes a Luer lock that can connect to a fluid container. In some examples, the connector 22 includes a valve 23 for controlling whether fluid is able to flow through connector 22. When the valve 23 is open, fluid can flow through connector 22 and the sheath lumen and when the valve 23 is closed, connector 22 prevents fluid flow therethrough. In some embodiments, the fluid container connected to connector 22 is configured to store contrast agent so that sheath mechanism 10 can deliver contrast agent through the sheath lumen.

The sheath handle 14, in some examples, includes an air valve 24 configured to move along a longitudinal axis 11 of the sheath mechanism 10. In some cases, it is beneficial for sheath mechanism 10 to prevent air from entering subcutaneous tissue of the patient during the procedure and/or prevent fluid loss from the pericardial space through the sheath lumen. In some examples, the air valve 24 is closed when occupying a first linear position relative to the rest of sheath handle 14 and is open when occupying a second linear position relative to the rest of sheath handle 14. When air valve 24 is closed, air is prevented from entering the proximal opening 18 of the sheath lumen and thus prevents air from entering the patient's body through the sheath lumen. When air valve 24 is closed, this can also prevent fluid from flowing through the sheath lumen, thus preventing an exodus of fluid through the sheath lumen from the pericardial space. The clinician can control whether the air valve 24 is open or closed by gripping the sheath handle 14 and moving the air valve 24 proximally or distally relative to the rest of the sheath handle 14 to transition between the open state and the closed state.

In some embodiments, sheath mechanism 10 is sized to receive the dilator mechanism 30 therein such that dilator mechanism 30 extends completely through the sheath lumen from the proximal opening 18 and beyond the distal opening 16. Dilator mechanism 30 includes a dilator body 32, a dilator handle 34 fixedly attached to a proximal end of dilator body 32, and a port 35. Dilator body 32, in some examples, is sized to be slidably received within the sheath lumen defined by sheath body 12 and sheath handle 14. As depicted in FIG. 1, the sheath lumen can slidably receive the dilator body 32 such that dilator handle 34 is proximal to the sheath lumen and a distal portion 38 of dilator body 32 is located distal to the distal opening 16 of the sheath lumen.

When the sheath mechanism 10 receives the dilator mechanism 30 within the sheath lumen, the clinician can maneuver and control the system 2 depicted in FIG. 1 by gripping the sheath handle 14 and the dilator handle 34. For example, the clinician can simultaneously advance sheath mechanism 10 and dilator mechanism 30 into the patient's subcutaneous tissue. The clinician can simultaneously withdraw sheath mechanism 10 and dilator mechanism 30 from the patient's subcutaneous tissue in some cases. Because the dilator mechanism 30 is slidably received within the sheath lumen of sheath mechanism 10, the clinician can control the dilator body 32 to move within the sheath lumen relative to sheath mechanism 10. For example, the clinician can advance dilator body 32 distally relative to sheath mechanism 10 and/or withdraw dilator body 32 proximally relative to sheath mechanism 10.

One way that the clinician can slide dilator body 32 within the sheath lumen is to grip the sheath handle 14 with one hand and grip the dilator handle 34 with another hand to move the sheath mechanism 10 receives the dilator mechanism 30 relative to each other. This can allow the clinician to withdraw the dilator mechanism 30 from the patient while leaving the sheath mechanism 10 in place, for example. Additionally, or alternatively, the clinician can grip the sheath handle 14 with one hand and grip the dilator handle 34 with another hand to simultaneously advance or simultaneously withdraw the sheath mechanism 10 and the dilator mechanism 30. In some embodiments, the sheath mechanism 10 and the dilator mechanism 30 can be removably attached to each other (e.g., locked to each other) when the dilator body 32 is received within the sheath lumen, allowing the clinician to simultaneously advance or simultaneously withdraw the sheath mechanism 10 and the dilator mechanism 30 by gripping only the dilator handle 34 or only the sheath handle 12. In some examples, sheath handle 12 includes a locking mechanism that can secure the dilator body 32 to the sheath handle 12 when the dilator body 32 is inserted into the sheath lumen.

As depicted in FIG. 1, a diameter of the dilator handle 34 can be larger than a diameter of proximal opening 18 such that dilator handle 34 limits distal advancement of the dilator mechanism 30 within the sheath lumen. This can ensure that the distal end of dilator mechanism 30 does not enter the sheath lumen so that the clinician can always grip part of the dilator mechanism 30 throughout the procedure. This allows the clinician to withdraw dilator mechanism 30 when appropriate and prevents a situation where the clinician cannot grasp the dilator mechanism 30 because its distal end is within the sheath lumen.

A greatest diameter of dilator body 32, in some examples, can be less than or equal to a lowest diameter of the sheath lumen in which the dilator body 32 is received. In some embodiments, a greatest diameter of dilator body 32 can be within a range from 12 French (Fr) to 28 Fr, such as 21 Fr. The dilator body 32, in some examples, includes a proximal portion and the distal portion 38. The proximal portion of dilator body 32, in some cases, can have the greatest diameter of the dilator body 32.

In some embodiments, the distal portion 38 of the dilator body 32 is tapered such that the diameter of dilator body 32 decreases moving distally along the distal portion 38. This can be a gradual tapering. For example, the outer surface of the dilator body 32 at distal portion 38 can form a shallow angle with the outer surface of dilator body 32 at the proximal portion (e.g., an angle within a range from 2 degrees to 8 degrees). This gradual tapering can ensure that when dilator body 32 advances through the patient's subcutaneous tissue, the distal portion 38 gradually enlarges an opening in the subcutaneous tissue.

As discussed above, the dilator handle 34 can include the port 35. This port 35 represents an opening into a dilator lumen that extends fully through the dilator mechanism 30 from the port 35 to a distal opening 36 of the dilator mechanism 30. In some examples, the dilator lumen can be sized to receive a guidewire 56 so that dilator mechanism 30 can advance into the patient over the guidewire 56 which passes through the dilator lumen. In some embodiments, the guidewire 56 can be advanced into the patient prior to the system 2 advancing into the patient such that the guidewire extends through the patient from an opening in the patient's skin to a targeted treatment site within the pericardium.

Using the guidewire can be beneficial so that the system 2 can arrive at the targeted treatment site easily along the guidewire 56. The dilator lumen can, in some examples, represent a fluid delivery lumen for delivering a fluid contrast agent to the targeted treatment site. For example, port 35 can include a connector sized to attach to a fluid contrast source configured for storing the fluid contrast agent. The dilator mechanism 30 can deliver the fluid contrast agent via the distal opening 36 of the dilator body 32.

Referring now to FIG. 2, in use during some implementations, the clinician can readily grasp the sheath handle 14 and/or the dilator handle 34 to simultaneously advance the sheath mechanism 10 and the dilator mechanism 30 along a guidewire 56 and into subcutaneous tissue of the patient. For example, the clinician can grasp the sheath handle 14 and the dilator handle 34 to simultaneously advance the sheath mechanism 10 and the dilator mechanism 30 over the guidewire 56 to the patient's heart 50. The heart 50 includes pericardium 52 and myocardium 54. The pericardium 52 is a membrane that surrounds myocardium 54 and can trap fluid in the pericardial sac between pericardium 52 and myocardium 54. The guidewire 56 can extend through opening 51 so that as sheath mechanism 10 and the dilator mechanism 30 advance over the guidewire 56, sheath mechanism 10 and the dilator mechanism 30 enter the pericardial sac.

For example, sheath mechanism 10 and the dilator mechanism 30 can simultaneously advance along the guidewire 56 so that a distal tip of dilator body 32 enters the opening 51 in the pericardium 52. The dilator body 32 can gradually enlarge the opening 51 as the dilator body 32 advances into the pericardial sac between the pericardium 52 and the myocardium 54. As depicted in FIG. 2, this gradual enlargement allows the distal tip of the sheath body 12 to enter the opening 51 which has been enlarged to a largest diameter of the dilator body 32. During simultaneous advancement of the sheath mechanism 10 and the dilator mechanism 30, the dilator mechanism 30 can be fully inserted into the sheath lumen such that the dilator handle 34 prevents further distal movement of the dilator mechanism 30 relative to the sheath mechanism 10 as depicted in FIG. 1.

In some cases, the clinician can advance the sheath mechanism 10 and the dilator mechanism 30 under direct visualization by one or more medical imaging systems. This medical imaging can allow the clinician to view an advancement of the sheath mechanism 10 and the dilator mechanism 30 in real time relative to a location of the patient's anatomy (e.g., heart 50). This can allow the clinician to determine when the sheath mechanism 10 and the dilator mechanism 30 are sufficiently positioned.

Referring now to FIG. 3, subsequent to advancing the sheath mechanism 10 and the dilator mechanism 30 simultaneously to the position depicted in FIG. 2, the clinician can withdraw the guidewire 56 and the dilator mechanism 30 from the pericardial sac and through the sheath lumen while maintaining a position of the distal tip of sheath body 12 within the opening 51. For example, the clinician can grip the sheath handle 14 with one hand and grip the dilator handle 34 with another hand to slide the dilator mechanism 30 proximally relative to sheath mechanism 10 while leaving sheath mechanism 10 in place. In some embodiments, the clinician can slide the dilator mechanism 30 proximally over the guidewire 56 so that the dilator mechanism 30 fully exits the sheath lumen through the proximal opening of the sheath lumen. Subsequent to removing the dilator mechanism 30, the clinician can, in some embodiments, remove the guidewire 56 by pulling the guidewire 56 proximally and out of the sheath lumen through the proximal opening 18 of the sheath lumen.

Figure 5:
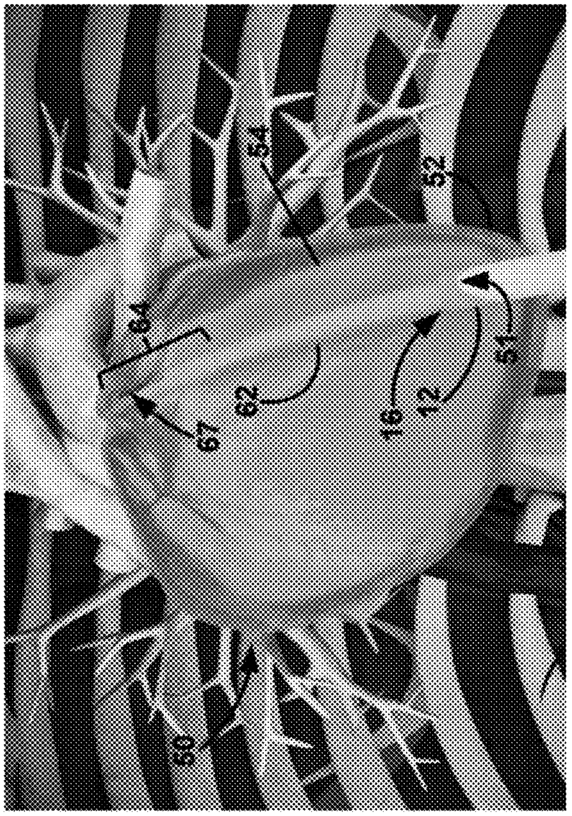
FIG. 5 illustrates the sheath mechanism and the catheter mechanism advanced to the targeted treatment site, the catheter mechanism including a cutting instrument in a retracted position.
Figure 6:
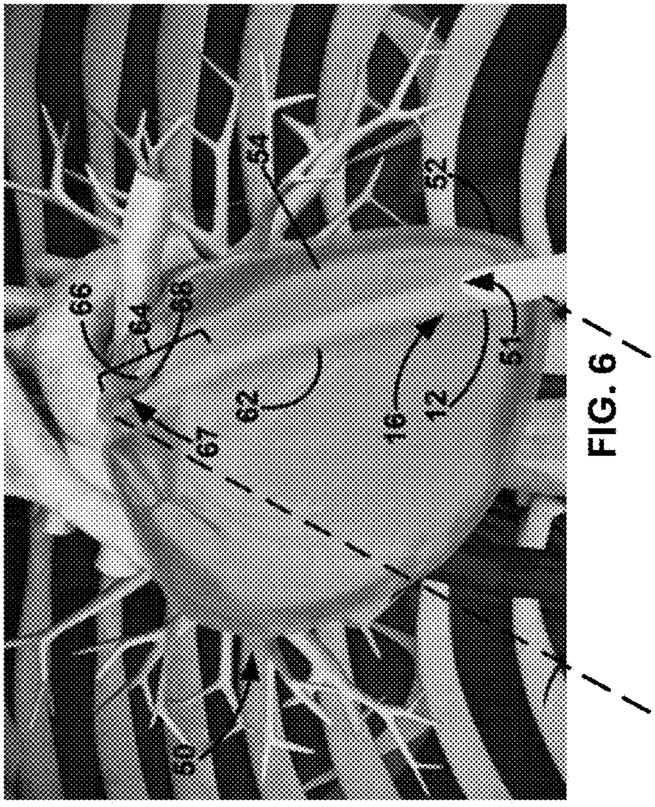
FIG. 6 illustrates the sheath mechanism and the catheter mechanism advanced to the targeted treatment site, the catheter mechanism including a cutting instrument in an actuated position.
Figure 4:
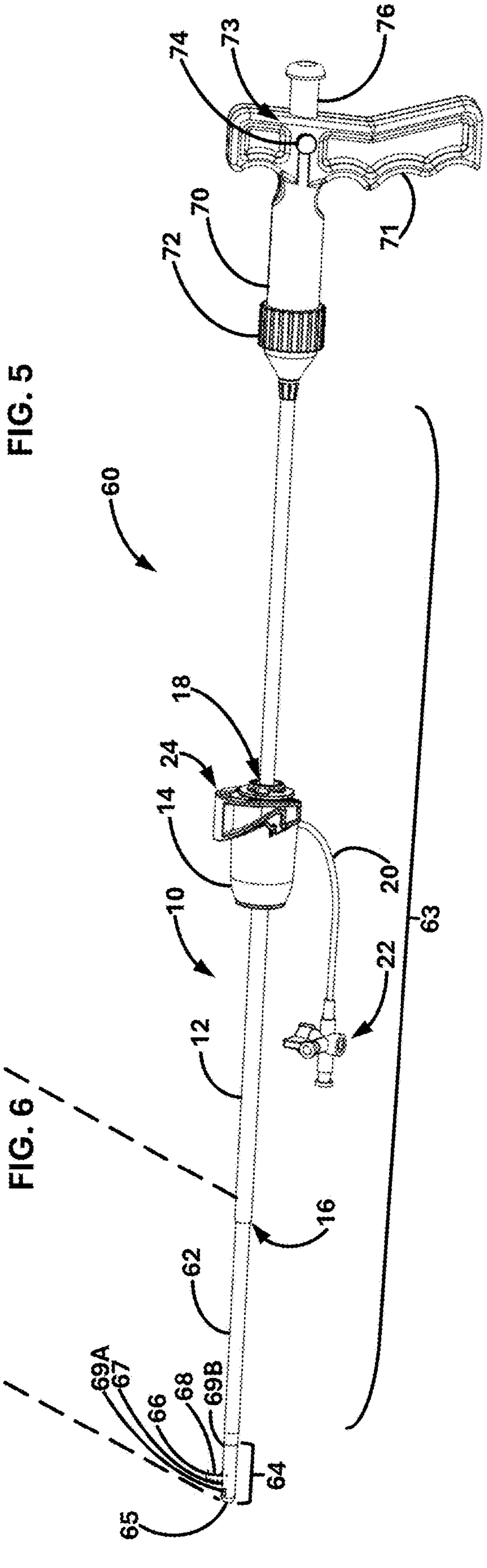
FIG. 4 illustrates the sheath mechanism and a catheter mechanism for performing a surgical procedure.

Referring now to FIGS. 4-6, some embodiments of a system 2 for performing a surgical procedure involving the pericardium to treat one or more cardiac conditions can include a sheath mechanism 10 and a catheter mechanism 60 (also simply referred to as a catheter). In some cases, system 2 can be configured to access and engage targeted tissue within a patient by advancing catheter mechanism 60 into a pericardial sac between the pericardium 52 and the myocardium 54 of a patient. As depicted in FIG. 4, the sheath lumen defined by sheath body 12 and sheath handle 14 can be sized to receive catheter mechanism 60 such that catheter mechanism 60 both extends distally beyond the distal opening 16 of the sheath lumen and catheter mechanism 60 extends proximally beyond the proximal opening 18 of the sheath lumen.

In some embodiments, catheter mechanism 60 can be inserted into the sheath lumen of sheath mechanism 10 when dilator mechanism 30 is not inserted into sheath mechanism 10. For example, catheter mechanism 60 can be inserted into the sheath lumen after dilator mechanism 30 is withdrawn from the sheath lumen. The same sheath mechanism 10 can be sized to receive both the dilator mechanism 30 and the catheter mechanism 60 at different times (e.g., the sheath lumen can receive one but not both of the dilator mechanism 30 and the catheter mechanism 60). The sheath lumen of sheath mechanism 10 can slidably receive catheter mechanism 60 such that catheter mechanism 60 is free to move proximally and or distally along the sheath lumen relative to sheath mechanism 10.

The catheter mechanism 60 can, in some examples, include a catheter body 62 and a catheter handle 70. The catheter handle 70 can be fixedly attached to a proximal end of catheter body 62. So configured, when the catheter body 62 is inserted into the sheath lumen through a proximal opening in the sheath lumen, the catheter body 62 is positioned proximal to the proximal opening of the sheath lumen. A clinician can grip catheter handle 70 to move catheter body 62. For example, a clinician can move the catheter body 62 relative to the sheath mechanism 10, move catheter body 62 and sheath mechanism 10 simultaneously, rotate catheter body 62 within the sheath lumen, rotate catheter body 62 and sheath mechanism 10 simultaneously, or any combination thereof. A greatest diameter of catheter body 62, in some examples, can be less than or equal to a lowest diameter of the sheath lumen in which the catheter body 62 is received. In some embodiments, a greatest diameter of catheter body 62 can be within a range from 12 Fr to 28 Fr, such as 21 Fr. In some examples, a largest diameter of catheter body 62 is the same as a largest diameter of dilator body 32, but this is not required. Catheter body 62 and dilator body 32 can have different diameters in some embodiments.

As discussed in greater detail below, the catheter mechanism 60, the catheter body 62, and the catheter handle 70 each share the same longitudinal axis 11, Which is also the same as the longitudinal axis 11 of the sheath mechanism 10.

In some embodiments, catheter body 62 is reinforced by a metal braid for stiffness. For example, a metal braid may run along an inside of catheter body 62 near an outer surface 62 of catheter body 62 such that the metal braid allows some bending of catheter body 62 but also resists bending of catheter body 62. In other words, this metal braid can increase an amount of force required to bend catheter body 62 as compared with an amount of force required to bend a catheter that is not reinforced by metal braid. This ensures that catheter body 62 can be deflected, for example, and also ensures that catheter body 62 does not bend too far from a straight configuration.

The catheter body 62, in some examples, includes a proximal portion 63 and a distal portion 64. In the position illustrated in FIG. 4, where the catheter body 62 is inserted within the sheath lumen, the sheath mechanism 10 is disposed over the proximal portion 63 of the catheter body 62, the distal portion 64 of the catheter body 62 is located distal to the sheath mechanism 10, and the catheter handle 70 is located proximal to the catheter body 62. The length of catheter body 62, in some examples, may be within a range from 40 cm to 70 cm (e.g., 54 cm). A length of the entire catheter mechanism 60, including the catheter body 62 and the catheter handle 70, in some embodiments, is within a range from 55 cm to 85 cm (e.g., 70 cm). In some examples, a length of catheter mechanism 60 is longer than a length of dilator mechanism 30 of FIG. 1. For example, a length of dilator mechanism 30 can be within a range from 15 cm to 40 cm (e.g., 31 cm) with dilator body 32 being within a range from 10 cm to 36 cm (e.g., 27.5 cm).

The distal portion 64 of catheter body 62, in some examples, includes a rounded distal tip 65. In some cases, rounded distal tip 65 has a rounded, semi-spherical shape so that distal tip 65 does not damage tissue as it advances through spaces in subcutaneous tissue. For example, the rounded shape of distal tip 65 can be without sharp or pronounced edges that present a higher risk of tissue damage. In some examples, a length of the distal portion 64 can be within a range from 1 cm to 5 cm (e.g., 2.8 cm).

In some embodiments, a cutting instrument 66 is movably mounted to the distal portion 64 of the catheter body 62. This cutting instrument 66 can include a blade 68 on one side of the cutting instrument 66. Cutting instrument 66 can be movably mounted to the distal portion 64 such that one end of the cutting instrument 66 is attached to the distal portion 64 at a hinge. This hinge can allow the cutting instrument 66 to rotate outwards from the distal portion 64 and rotate inwards towards the distal portion 64.

For example, the cutting instrument 66 can be configured to occupy a retracted position where cutting instrument 66 is fully within an outer housing of the catheter body 62 (e.g., within distal portion 64) so that cutting instrument 66 is substantially parallel to a longitudinal axis 11 of the catheter body 62. The cutting instrument 66 can also occupy an actuated position where the cutting instrument extends outward from the distal portion 64 of the catheter body 62 such that cutting instrument 66 forms an angle with the longitudinal axis 11 of catheter body 62.

The cutting instrument 66 can transition from the retracted position to the actuated position by rotating about the hinge in a first rotational direction so that the cutting instrument 66 extends outward from an opening 67 in the outer housing of the distal portion 64 of catheter body 62. The cutting instrument 66 can transition from the actuated position to the retracted position by rotating about the hinge in a second rotational direction, opposite the first rotational direction, so that the cutting instrument 66 retracts inward through opening 67 in the outer housing of the distal portion 64.

Blade 68 of cutting instrument 66 is positioned to cut tissue when the cutting instrument 66 is in the actuated position. For example, in the actuated position, blade 68 is outside of the outer housing of catheter body 62 and exposed to tissue outside of the catheter body 62. When catheter body 62 moves with cutting instrument 66 in the actuated position, this movement can cause blade 68 to cut tissue. On the other hand, blade 68 is prevented from cutting tissue when the cutting instrument 66 is in the retracted position. For example, in the retracted position, the cutting instrument 66 including the blade 68 is fully within the outer housing of catheter body 62. When catheter body 62 moves with cutting instrument 66 in the retracted position, the blade 68 is not exposed to tissue outside of the catheter body 62 and movement of catheter body 62 does not cause blade 68 to cut tissue.

In the embodiment of FIG. 4, cutting instrument 66 is in the actuated position with the blade 68 exposed. The cutting instrument 66 can transition from the actuated position depicted in FIG. 4 to the retracted position by rotating counterclockwise (from the perspective of FIG. 4) into the opening 67 in the outer housing of catheter body 62. The cutting instrument 66 can transition from the retracted position to the actuated position depicted in FIG. 4 by rotating clockwise (from the perspective of FIG. 4) out of the opening 67 in the outer housing of catheter body 62 so that the cutting instrument 66 forms an angle with a longitudinal axis 11 of the catheter body 62. In certain embodiments, angle is approximately 90 degrees, such that the cutting instrument 66 is approximately perpendicular to the longitudinal axis 11 of the catheter body 62.

The blade 68 can be located on one side of the cutting instrument 66 (e.g., on the right side of the cutting instrument 66 from the perspective of FIG. 4). This means that in some embodiments, blade 68 of cutting instrument 66 can be configured to cut tissue when moving in a first direction (e.g., rightwards from the perspective of FIG. 4) without cutting tissue when moving in a second direction (e.g., leftwards from the perspective of FIG. 4) opposite the first direction. This can ensure that a clinician can make one or more cuts by using one kind of movement (e.g., moving the catheter mechanism 60 proximally relative to sheath mechanism 10).

In some examples, the hinge at which cutting instrument 66 is attached to the distal portion 64 of the catheter body 62 is located within the outer housing of catheter body 62. This ensures that cutting instrument 66 can fully retract within the catheter body 62 through opening 67 so that no part of cutting instrument 66 is outside of the outer housing of catheter body 62 when cutting instrument 66 is in the retracted position.

In some embodiments, the cutting instrument 66 can define a fluid opening at a tip of the cutting instrument 66 that is in fluid connection to a fluid lumen within the catheter body 62. In some examples, the catheter mechanism 60 can deliver a fluid contrast agent to a targeted region via the fluid opening at the tip of the cutting instrument 66. The fluid opening at the tip of the cutting instrument 66, in some cases, can be in fluid communication with the fluid lumen within the catheter body 62 when the cutting instrument 66 is in the actuated position.

In some examples, the fluid contrast agent delivered via the fluid opening can provide contrast for direct visualization of the catheter mechanism 60 using one or more medical imaging systems. For example, the fluid contrast agent can make anatomy of the patient (e.g., the pericardium and the myocardium) appear in the medical imaging in contrast with the catheter mechanism 60 so that the clinician can view a location of the catheter mechanism 60 relative to the patient's anatomy in real time.

The distal portion 64 of the catheter body 62, in some examples, can include electrodes 69A-69B (collectively, "electrodes 69"). These electrodes 69 can be positioned on the outer housing of the catheter mechanism 60 and configured to deliver electrical stimulation to a targeted tissue area and/or sense electrical signals at the targeted tissue area. For example, the electrodes 69 can represent a bipolar electrode system where the electrode 69A delivers electrical stimulation that returns via the electrode 69B. In another embodiment, the electrodes 69 can represent a monopolar electrode system, where one of the electrodes 69A-69B delivers electrical stimulation and the electrical stimulation returns via a return pad positioned on a patient's body (not shown).

Electrode 69A and electrode 69B can each be connected to a conductor that extends through the outer housing of catheter body 62 and is connected to circuitry. For example, a pulse generator can deliver electrical stimulation via electrode 69A (e.g., a stimulation electrode) and/or sense signals via electrode 69B (e.g., a sense electrode).

In some examples, the electrical signals delivered via the electrodes 69 can be for sensing a proximity of one or more nerves (e.g., the phrenic nerve) to the distal portion 64 of the catheter body 62. For example, electrical stimulation delivered via the electrode 69A can stimulate the phrenic nerve. Electrical signals sensed via the electrode 69B can reflect activity of the phrenic nerve that indicates a proximity of the phrenic nerve to distal portion 64. The electrode 69B can be connected to sensing circuitry configured to receive the electrical signals sensed by the electrode 69B to determine the proximity of the phrenic nerve to distal portion 64 of the catheter mechanism 60.

Because it is beneficial to avoid damaging the phrenic nerve in making a cut to the pericardium 52, it can be beneficial to sense a proximity of the phrenic nerve to distal portion 64. This allows the clinician to avoid cutting tissue when the phrenic nerve is too close to the distal portion 64 to avoid cutting the phrenic nerve. In some cases, the contrast agent delivered via the tip of the cutting instrument 66 can be beneficial for determining a proximity of the phrenic nerve to the distal portion 64. For example, the contrast agent can make the patient's anatomy (e.g., heart 50, pericardium 52, myocardium 54) more visible in medical imaging relative to the distal portion 64 of catheter body 62, thus giving the physician a better sense of the position of distal portion 64 relative to the phrenic nerve. Even if the phrenic nerve is not visible in medical imaging, the clinician can use medical imaging in combination with signals sensed by the electrodes 69 to assess a proximity of the phrenic nerve to the distal portion 64.

The distal portion 64 is not limited to including a single bipolar electrode system. In some embodiments, distal portion 64 includes more than one pair of bipolar electrodes. In some embodiments, the distal portion 62 of catheter body 62 includes one or more unipolar electrodes that deliver stimulation and/or sense electrical signals. In some embodiments, the distal portion 64 includes more than two electrodes or less than two electrodes. In some embodiments, catheter mechanism 60 includes one or more electrodes that are located separate from distal portion 62 of catheter body 62 (e.g., located on catheter body 62 proximal to the distal portion 64. The catheter body 62 is not limited to including one conductor for each electrode on the distal portion 64 of catheter body 64. In some cases, more than one (e.g., two) conductors can be connected to each electrode located on catheter body 62 (e.g., two conductors connected to electrode 69A and two conductors connected to electrode 69B).

The catheter handle 70 of the catheter mechanism 60 can be sized to be held by a clinician so that the clinician can control one or more movements of catheter mechanism 60. For example, catheter handle 70 includes finger grips 71 that are sized for fingers of a human user (e.g., a clinician) to grip the catheter handle 70 with one hand. In the embodiment of FIG. 4, the finger grips 71 include four finger grips with one finger grip above a main section of the catheter handle 70 and three finger grips below the main section of the catheter handle, but this is not required. In other embodiments, the catheter handle 70 can include more than or fewer than four finger grips 71. In some cases, a clinician can grip the catheter handle 70 with one hand and grip the sheath handle 14 with another hand, both the catheter handle 70 and the sheath handle 14 being outside of the patient while portions of the catheter body 62 and the sheath body 12 are inside of the patient. This allows the clinician to independently maneuver each of the sheath mechanism 10 and the catheter mechanism 60 to complete a surgical procedure to cut the pericardium 52.

In some cases, a clinician can rest the catheter handle 70 in the sterile field and finger grips 71 will stabilize the catheter handle 70, limiting rotation of the system 2. In some cases, a clinician can reference the finger grips 71 as an orientation aid, in addition to medical imaging, for the location of the opening 67 and the cutting instrument 66.

The catheter handle 70 can include a deflection actuator 72 for controlling a deflection of the distal portion 64 of the catheter body 62. For example, deflection actuator 72 can be connected to a pull wire 82 (see FIG. 17) that runs through the catheter mechanism 60 from the catheter handle 70 to the distal portion 64. The pull wire 82 can be connected to the catheter body 62 at a location within the outer housing at distal portion 64. This pull wire 82 can tighten and/or loosen within the catheter mechanism 60 based on a rotational movement of deflection actuator 72 about the main portion of the catheter handle 70 (e.g., about a longitudinal axis 11 of the catheter mechanism 60).

In some examples, deflection actuator 72 can decrease a length (e.g., tighten) of the pull wire 82 by rotating in a first rotational direction, and deflection actuator 72 can increase a length (e.g., loosen) the pull wire 82 by rotating in a second rotational direction opposite the first rotational direction. For example, a rotation of deflection actuator 72 in the first rotational direction can apply tension to the pull wire 82, causing the pull wire 82 to tighten, and applying pressure to distal portion 64 that causes distal portion 64 to deflect relative to a longitudinal axis 11 of the catheter mechanism 60. This deflection can result due to the catheter body 62 bending from a straight position to a curved position due to the tightening of the pull wire 82 caused by the rotation of the deflection actuator 72. Rotation of deflection actuator 72 in the second rotational direction can cause the pull wire 82 to loosen, relieving pressure to the distal portion 64. This can allow the catheter body 62 to return from the curved position to the straight position.

The clinician can control a degree of deflection of the distal portion 64 by controlling a degree to which deflection actuator 72 rotates. In an embodiment, the deflection actuator 72 can be a knob that is rotatably attached to an outer surface of the catheter handle 70. So configured, the knob applies tension to the pull wire 82 based on rotational movement of the knob about catheter handle 70 to cause the distal portion 64 of the catheter mechanism 60 to deflect relative to the longitudinal axis 11 of the catheter mechanism 60. In certain embodiments, the knob is configured to rotate between a first rotational position corresponding to no deflection of the distal portion 64 of the catheter mechanism 60 and a second rotational position corresponding to deflection of the distal portion 64 of the catheter mechanism 60.

The configuration of the deflection actuator is not limited and, in further embodiments, the deflection actuator can be any kind of actuator that is configured for actuation to tighten or loosen the pull wire 82 (e.g., a knob, switch, lever, slider, etc.)

In additional embodiments, the catheter mechanism 60 is not limited to including a single pull wire 82 connected to a single deflection actuator 72. In some examples, the catheter mechanism 60 includes more than one pull wire, each pull wire connected to a respective deflection actuator on catheter handle 70. Each pull wire of the one or more pull wires can be connected to a location within the outer housing of catheter body 62 such that the pull wire can deflect the catheter body 62 in a respective direction. For example, a first pull wire connected to the deflection actuator 62 and connected to a first location on the distal portion 64 can deflect the catheter body 62 in a first direction (e.g., in a direction corresponding to a location of the opening 67) and a second pull wire connected to the deflection actuator 62 and connected to a second location on the distal portion 64 can deflect the catheter body 62 in a second direction (e.g., in a direction opposite a location of the opening 67). Additional pull wires, in some embodiments, can be positioned to deflect the catheter body 62 in additional directions.

In some embodiments, the catheter handle 70 includes a blade actuator 73 connected to a mandrel 86 (see FIG. 17) within the outer housing of the catheter mechanism 60. The mandrel 86 can run along the catheter mechanism 60 from the catheter handle 70 to the distal portion 64. The mandrel 86 can attached to the blade 68 so that, based on movement of the blade actuator 73, the mandrel 86 causes the blade 68 to move from the retracted position to the actuated position In an example, the blade actuator 73 can include a safety mechanism 74 and a transition mechanism 76. In some examples, the safety mechanism 74 is rotatably attached to the outer surface of the catheter handle 70 and is configured to rotate between an engaged position and a disengaged position. The transition mechanism 76 can be slidably attached to the mandrel 86.

When the safety mechanism 74 is in the disengaged position, the transition mechanism 76 can move the mandrel 86 to transition the cutting instrument 66 from the retracted position to the actuated position and/or move to transition the cutting instrument 66 from the actuated position to the retracted position.

On the other hand, when the safety mechanism 74 is in the engaged position, the safety mechanism 74 can physically prevent the transition mechanism 76 from moving to transition the cutting instrument 66 from the retracted position to the actuated position and/or move to transition the cutting instrument 66 from the actuated position to the retracted position.

In this manner, the safety mechanism 74 can lock the cutting instrument 66 in the actuated position or lock the cutting instrument 66 in the retracted position by placing the safety mechanism 74 in the engaged position and the safety mechanism 74 can allow the cutting instrument 66 to move between the retracted position and the actuated position by placing the safety mechanism 74 in the disengaged position.

The engaged position and the disengaged position of safety mechanism 74 can represent rotational positions of the safety mechanism 74. For example, safety mechanism 74 can be a rotatable element that is configured to rotate about an axis that is perpendicular to a longitudinal axis 11 of catheter handle 70. As depicted in FIG. 4, safety mechanism 74 is a round knob that is mounted on a side of the catheter handle 70. In some cases, the round knob of safety mechanism 74 can be connected to a handle or another element that can be rotated to cause the knob to rotate on the side of the catheter handle 70. In any case, the safety mechanism 74 can be rotated between a first rotational position corresponding to an engaged state and a second rotational position corresponding to a disengaged state. The safety mechanism 74 can rotate to transition between the first rotational position and the second rotational position in order to transition between the engaged state and the disengaged state.

Figure 21:
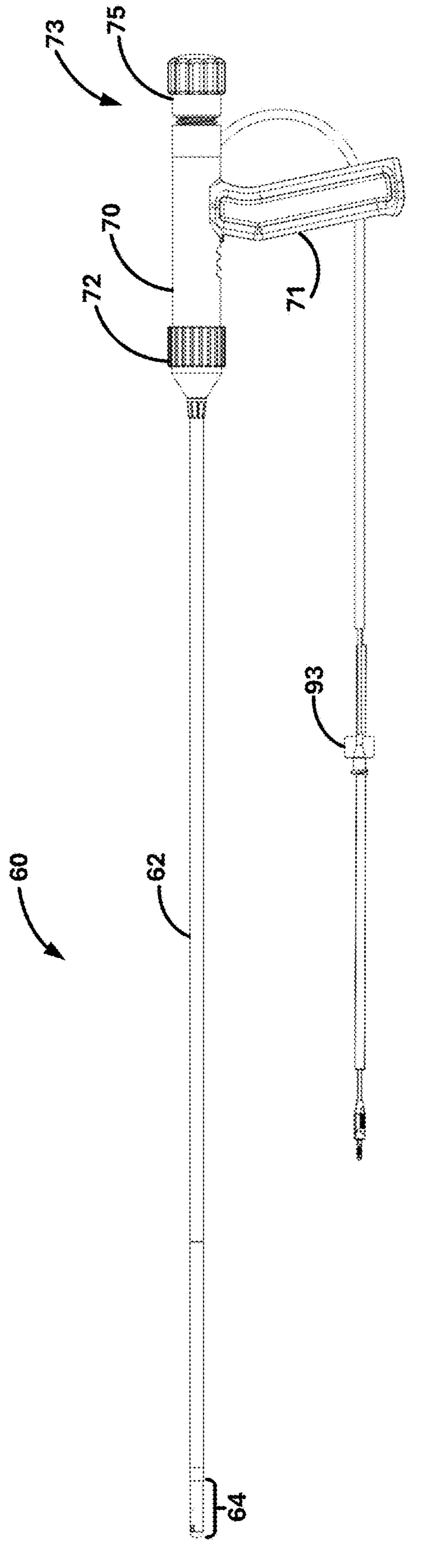
FIG. 21 illustrates an embodiment of the catheter mechanism including a deployment actuator.

Embodiments of the blade actuator 73 are not limited to including the safety mechanism 74 and the transition mechanism 76. In other embodiments, illustrated in FIG. 21, the blade actuator 73 can include a deployment actuator 75 and the transition mechanism 76. The configuration of the transition mechanism 76 can be the same as that discussed above.

In some examples, deployment actuator 75 can be a round knob that is rotatably fixed to the catheter handle 70 such that it encompasses the transition mechanism 76 and controls movement of the transition mechanism 76. In some embodiments, the deployment actuator 75 is a self-locking and self-locks with the catheter handle 70. For example, rotation of the deployment actuator 75 in a first rotational direction can move the transition mechanism 76 to transition the cutting instrument 66 from the retracted position to the actuated position. Rotation of the deployment actuator 75 in a second rotational direction, opposite the first rotational direction, can move the transition mechanism 76 to transition the cutting instrument 66 from the actuated position to the retracted position.

The clinician can control a degree to which the cutting instrument 66 actuates and/or retracts by controlling a degree to which deployment actuator 75 rotates. Based on the self-locking feature of deployment actuator 75, the transition mechanism 76 and the cutting instrument 66 are prevented from changing position when the deployment actuator is not in rotation. This means that the deployment actuator 75 can lock the cutting instrument 66 in the actuated position or lock the cutting instrument 66 in the retracted position when it is not engaged (e.g. not rotated) and the deployment actuator 75 can allow the cutting instrument 66 to move between the retracted position and the actuated position when it is engaged (e.g. rotated). The deployment actuator 75 is not limited to being a knob that rotates about the catheter handle 70. In some cases, the deployment actuator 75 can be any kind of actuator such as a knob, switch, lever, or slider that is configured to move the transition mechanism 76.

In other embodiments, blade actuator 73 can include a rotation actuator 97 and a deployment mechanism 98. For example, the rotation actuator 97 can be connected to the mandrel 86 within the outer housing of the catheter mechanism 60. The mandrel 86 can be attached to the blade 68 through the deployment mechanism 98 so that the deployment mechanism 98 causes the blade to move from the retracted position to the actuated position based on movement of the rotation actuator 97.

In some examples, rotation actuator 97 can be a round knob that is rotatably attached to catheter handle 70. The rotation actuator 97 an be connected to the mandrel 86 that runs along the catheter mechanism 60 from the catheter handle 70 to the distal portion 64. The mandrel 86 can be connected to the deployment mechanism 98, positioned in the distal portion 64, such that rotation of the rotation actuator 97 can rotate the mandrel 86 and, subsequently, the deployment mechanism 98.

The rotation of deployment mechanism 98 can transition the cutting instrument 66 from the retracted position to the actuated position and/or transition the cutting instrument 66 from the actuated position to the retracted position. For example, rotation of the rotation mechanism 98 in a first rotational direction can rotate the deployment mechanism 98 to transition the cutting instrument 66 from the retracted position to the actuated position. Rotation of the rotation mechanism 98 in a second rotational direction, opposite the first rotational direction, can rotate the deployment mechanism 98 to transition the cutting instrument 66 from the actuated position to the retracted position.

The clinician can control a degree to which the cutting instrument 66 actuates and/or retracts by controlling a degree to which rotation actuator 97 rotates. The rotation actuator 97, the deployment mechanism 98, or both can be self-locking such that cutting instrument 66 is prevented from changing position when the rotation actuator 97 and the deployment mechanism 98 are not in rotation. This means that the rotation actuator 97 and/or deployment mechanism 98 can lock the cutting instrument 66 in the actuated position or lock the cutting instrument 66 in the retracted position when it is not engaged (e.g. not rotated) and the rotation actuator 97 and/or the deployment mechanism 98 can allow the cutting instrument 66 to move between the retracted position and the actuated position when it is engaged (e.g. rotated).

In further embodiments, the rotation actuator 97 is not limited to being a knob that rotates about catheter handle 70. In some cases, the rotation actuator 97 can be any kind of actuator, such as a knob, switch, lever, or slider.

Transitioning the cutting instrument 66 between the actuated position and the retracted position involves moving the mandrel 86 within the catheter body 62. The mandrel 86 is connected at a distal end to the cutting instrument 66 so that movements of the mandrel 86 causes the cutting instrument 66 to rotate about a hinge. For example, transitioning the cutting instrument 66 from the retracted position to the actuated position can involve the safety mechanism 74 rotating to the disengaged position and the transition mechanism 76 advancing distally along the longitudinal axis 11 of catheter handle 70 to cause the mandrel 86 to rotate the cutting instrument 66 out of the opening 67 and into the actuated position.

In some cases, based on the cutting instrument 66 being transitioned from the retracted position to the actuated position, the safety mechanism 74 can rotate from the disengaged position to the engaged position to lock the cutting instrument 66 in the actuated position. Transitioning the cutting instrument 66 from the actuated position to the retracted position can involve the safety mechanism 74 rotating from the engaged position to the disengaged position and the transition mechanism 76 advancing proximally along the longitudinal axis 11 of the catheter handle 70 to cause the mandrel 86 to retract the cutting instrument 66 into the opening 67. In some cases, based on the cutting instrument 66 being transitioned from the actuated position to the retracted position, the safety mechanism 74 can rotate from the disengaged position to the engaged position to lock the cutting instrument 66 in the retracted position.

In some embodiments, transitioning the cutting instrument 66 from the retracted position to the actuated position can involve rotating the deployment actuator 75 in a first rotational direction to advance the transition mechanism 76 distally along the longitudinal axis 11 of the catheter handle 70 to cause the mandrel 86 to rotate the cutting instrument 66 out of the opening 67 and into the actuated position. Transitioning the cutting instrument 66 from the actuated position to the retracted position can involve the deployment actuator 75 rotating in a second rotational direction opposite the first rotational direction to advance the transition mechanism 76 proximally along the longitudinal axis 11 of the catheter handle 70 to cause the mandrel 86 to retract the cutting instrument 66 into the opening 67. In any case, after the deployment actuator 75 is rotated, the cutting instrument 66 will remain in position until deployment actuator 75 is rotated by the clinician again due to its self-locking properties.

In some embodiments, transitioning the cutting instrument 66 from the retracted position to the actuated position can involve rotating the rotation actuator 97 in a first rotational direction to rotate the mandrel 86 and the deployment mechanism 98 to cause the cutting instrument 66 to rotate out of opening 67 into the actuated position. Transitioning the cutting instrument 66 from the actuated position to the retracted position can involve the rotation actuator 97 rotating in a second rotational direction opposite the first rotational direction to rotate the mandrel 86 and the deployment mechanism 98 causing the cutting instrument 66 to rotate into opening 67. In any case, after the rotation actuator 97 is rotated, the cutting instrument 66 will remain in position until the rotation actuator is rotated by the user again due to the self-locking properties of the rotation actuator 97 and/or the deployment mechanism 98.

Referring now to FIG. 5, in use during some implementations, while the distal tip of the sheath body 12 is located inside of the opening 51 in the pericardium 52, the clinician can readily grasp the catheter handle 70 and insert the catheter body 62 into the proximal opening 18 of the sheath lumen. In some cases, the clinician can grip the sheath handle 14 with one hand and grip the catheter handle 70 with another hand to provide control over both of the sheath mechanism 10 and the catheter mechanism 60. The clinician can advance the catheter body 62 through the sheath lumen while maintaining the distal tip of sheath body 12 in place within the opening 51 in the pericardium 52. The clinician can advance the catheter body 62 through the sheath lumen so that the distal portion 64 of the catheter body 62 passes distally out of the distal opening 16 of the sheath lumen and into the space between the pericardium 52 and the myocardium 54 (e.g., the space between the fibrous pericardium and the serous pericardium), as depicted in FIG. 5. The clinician can advance the distal portion 64 of the catheter body 62 to reach the position depicted in FIG. 5, with the distal tip of sheath body 12 remaining in place within the space between the fibrous pericardium and the serous pericardium (e.g., between the outer layer of the pericardium 52 (the fibrous pericardium) and the myocardium 54).

As illustrated in FIG. 5, the cutting instrument 66 occupies the retracted position as the distal portion 64 of the catheter body 62 advances through the sheath lumen and advances beyond the distal opening 16 of the sheath lumen to the position of FIG. 5. When the distal portion 64 is advancing to a position to make a cut in the pericardium 52, it is beneficial for cutting instrument 66 to remain in the retracted position so that tissue is not cut until the distal portion 64 is positioned sufficiently to cut the pericardium 52. Another benefit of the cutting instrument 66 remaining in the retracted position while the catheter body 62 advances through the sheath lumen and the space between the pericardium 52 and the myocardium 54 is that the cutting instrument 66 can advance more easily while the cutting instrument 66 is retracted as opposed to when the cutting instrument 66 is actuated. This is because the distal portion 64 is streamlined with a rounded tip when the cutting instrument 66 is retracted, whereas in the actuated state the cutting instrument 66 extends outward from the catheter body 62.

Referring now to FIG. 6, when the distal portion 64 of the catheter body 62 is advanced to the position depicted in FIGS. 5-6, the clinician can use the blade actuator 73 to transition the cutting instrument 66 from the retracted position to the actuated position. As depicted in FIG. 6, the cutting instrument 66 is in the actuated position with the cutting instrument 66 extending outward from the catheter body 62. When the cutting instrument 66 is in the actuated position, the blade 68 faces downward from the perspective of FIG. 6 towards a direction of the sheath body 12. This is because in the position of FIG. 6, distal portion 64 can be fully extended. When the cutting instrument 66 is withdrawn distally back towards the sheath body 12, this causes the blade 68 to cut the pericardium 52.

In some examples, to transition the cutting instrument 66 from the retracted position to the actuated position, the clinician can control the blade actuator 73 including the safety mechanism 74 and the transition mechanism 76 to cause the cutting instrument 66 to transition from the retracted position to the actuated position. In one example, the clinician can control the safety mechanism 74 to transition from being engaged to being disengaged. This can allow transition mechanism 76 to move, thus causing the mandrel 86 within the catheter mechanism 60 to move, transitioning cutting instrument 66 from the retracted position to the actuated position. For example, the clinician can push transition mechanism 76 inwards while the safety mechanism 74 is disengaged, moving the mandrel 86 relative to catheter body 62. This movement of the mandrel 86 causes the cutting instrument 66 to pivot about a hinge out of opening 67 so that cutting instrument 66 forms an angle with a longitudinal axis 11 of the catheter body 62. In some examples, subsequent to transitioning the cutting instrument 66 from the retracted position to the actuated position, the clinician can control the safety mechanism 74 to transition from being disengaged to being engaged. This can lock cutting instrument 66 in the actuated position and prevent the cutting instrument 66 from folding back into the opening 67 until the clinician controls the cutting instrument 66 to retract.

In some examples, to transition the cutting instrument 66 from the retracted position to the actuated position, the clinician can control the blade actuator 73 including the deployment actuator and the transition mechanism 76 to cause the cutting instrument 66 to transition from the retracted position to the actuated position. In one example, the clinician can control deployment actuator to move transition mechanism 76, thus causing the mandrel 86 within the catheter mechanism 60 to move, transitioning the cutting instrument 66 from the retracted position to the actuated position. For example, the clinician can rotate the deployment actuator clockwise, moving the mandrel 86 relative to catheter body 62. This movement of the mandrel 86 causes the cutting instrument 66 to pivot about a hinge out of the opening 67 so that cutting instrument 66 forms an angle with a longitudinal axis 11 of the catheter body 62. The cutting instrument 66 will lock in position once the clinician is no longer controlling the deployment actuator due to the self-locking feature of the deployment actuator and prevent the cutting instrument 66 from folding back into the opening 67 until the clinician controls deployment actuator to retract the cutting instrument 66.

In some examples, to transition the cutting instrument 66 from the retracted position to the actuated position, the clinician can control the blade actuator 73 including the rotation actuator and the deployment mechanism to cause the cutting instrument 66 to transition from the retracted position to the actuated position. In one example, the clinician can control the rotation actuator, thus causing the mandrel 86 within catheter mechanism 60 and the deployment mechanism within distal portion 64 to rotate, transitioning cutting instrument 66 from the retracted position to the actuated position. For example, the clinician can rotate rotation actuator clockwise, which can also rotate the mandrel 86 and deployment mechanism 98. This rotation of the deployment mechanism causes the cutting instrument 66 to pivot about a hinge out of opening 67 so that cutting instrument 66 forms an angle with the longitudinal axis 11 of the catheter body 62. This cutting instrument will lock in position once the clinician is no longer controlling the rotation actuator due to the self-locking feature of the rotation actuator and/or the deployment mechanism and prevent the cutting instrument 66 from folding back into the opening 67 until the clinician controls the rotation actuator to retract the cutting instrument 66.

Figure 7:
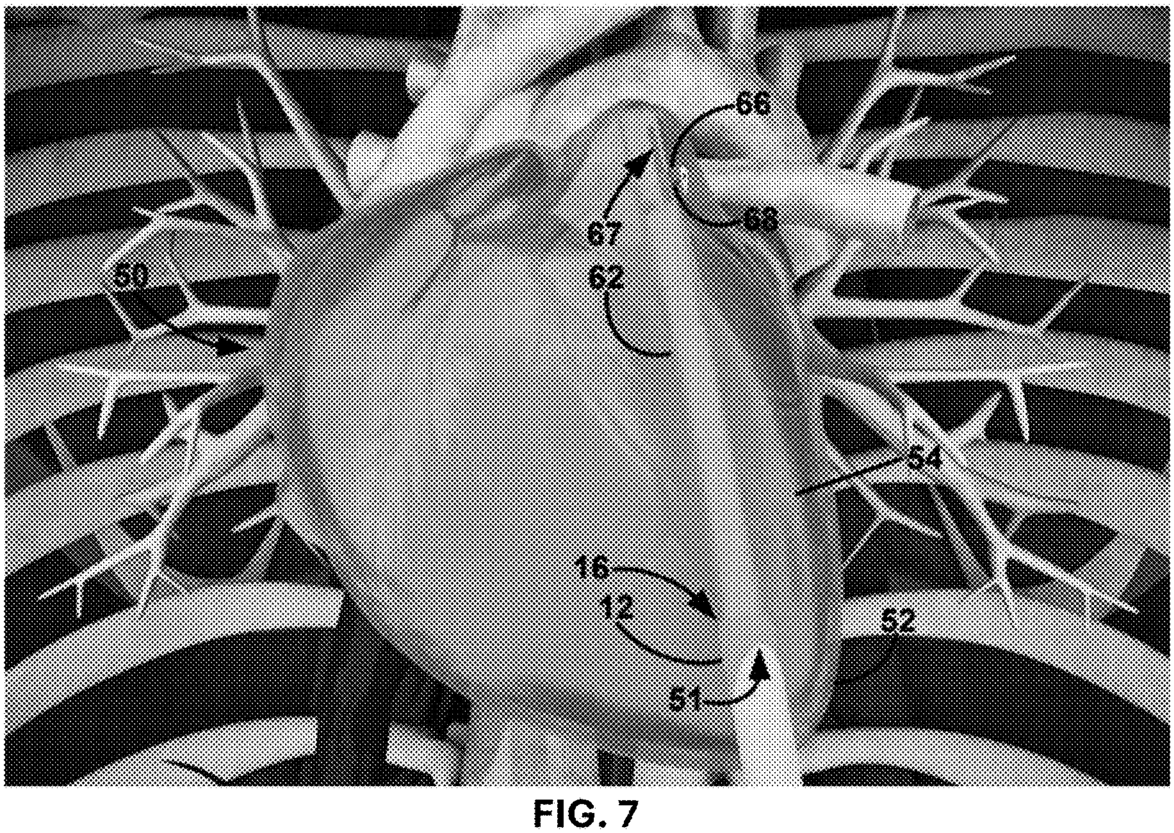
FIG. 7 illustrates the sheath mechanism and the catheter mechanism advanced to the targeted treatment site, the catheter mechanism including a cutting instrument in the actuated position and deflected to pierce the pericardium.

Referring now to FIG. 7, the clinician can control the deflection actuator 72 to deflect the distal portion 64 within the space between the pericardium 52 and the myocardium 54 (e.g., within the space between the fibrous pericardium and the serous pericardium) when the cutting instrument 66 is in the actuated position as depicted in FIG. 6. In some cases, this deflection of the distal portion 64 causes the blade 68 to pierce the pericardium 52 (e.g., pierce the fibrous pericardium), but this is not required. In some cases, the blade 68 first pierces the pericardium 52 (e.g., pierces the fibrous pericardium) when the cutting instrument 66 transitions from the retracted position to the actuated position as depicted in FIG. 6.

To control the deflection actuator 72 to deflect the distal portion 64 within the space between the pericardium 52 and the myocardium 54 (e.g., a space between the fibrous pericardium and the serous pericardium), the clinician can rotate the deflection actuator 72 about a longitudinal axis 11 of the catheter body 62. This can tighten the pull wire 82 within the outer housing of the catheter body 62 to apply pressure to the distal portion 64 of catheter body 62. In cases where the distal portion 64 is within a space between the fibrous pericardium and the serous pericardium, deflecting the catheter body 62 can cause the distal portion 64 to apply pressure to the fibrous pericardium in a way that separates the fibrous pericardium from the serous pericardium.

The pressure associated with the tightening of the pull wire 82 can cause the catheter body 62 to bend outwards (deflect) away from the myocardium 54. In some examples, the pull wire 82 can be configured so that distal portion 64 deflects in the direction of the opening 67 in the distal portion 64 of the catheter body 62. This means that the clinician can orient the catheter body 62 properly so that the opening 67 is faced outwards away from myocardium 54 and towards the pericardium 52 prior to transitioning the cutting instrument 66 from the retracted position to the actuated position. For example, the catheter body 62 can rotate within the sheath lumen. The clinician can grip catheter handle 70 to rotate the catheter body 62 so that the opening 67 is faced outwards towards the pericardium 52. In some cases, pericardium 52 includes two layers including the fibrous pericardium and the serous pericardium. Deflecting the catheter body 62 outwards away from the myocardium 64 can, in some examples, cause the fibrous pericardium to be separated from the serous pericardium.

Figure 8:
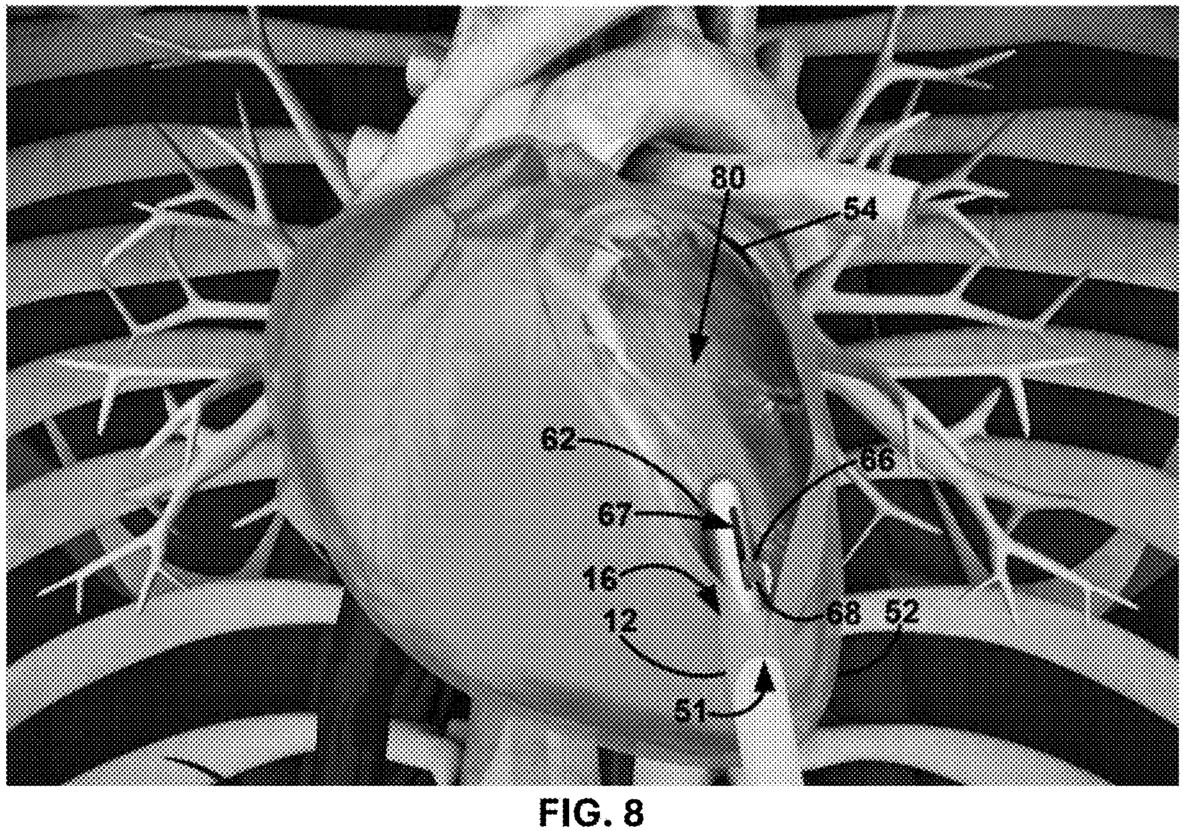
FIG. 8 illustrates the sheath mechanism and the catheter mechanism advanced to the targeted treatment site, the catheter mechanism at least partially retracted to cut the pericardium with the cutting instrument in the actuated position.

Referring now to FIG. 8, in use during some implementations, the clinician can withdraw the catheter body 62 proximally and into the sheath lumen defined by sheath body 12 while the cutting instrument 66 is in the actuated position and while the distal tip of sheath body 12 remains within the opening 51 in the pericardium 52. In some cases, while the clinician withdraws the catheter body 62 while cutting instrument 66 is in the actuated position, the blade actuator 73 on catheter handle 70 can maintain the cutting instrument 66 by preventing the cutting instrument 66 from returning to the retracted position within the catheter body 62. One way that the blade actuator 73 maintains the cutting instrument 66 in the actuated position is by the safety mechanism 74 being secured in the engaged position.

Another way that the blade actuator 73 maintains the cutting instrument 66 in the actuated position is by the self-locking feature of the deployment actuator, the rotation actuator, and/or the deployment mechanism. When the safety mechanism 74 is secured in the engaged position or the self-locking deployment actuator, rotation actuator, and/or deployment mechanism is used; this prevents the transition mechanism 76 from moving and thus prevents the mandrel 86 within the catheter mechanism 60 from moving. In any case, this maintains cutting instrument 66 in the actuated position as catheter body 62 withdraws proximally into the sheath lumen defined by sheath body 12.

As catheter body 62 withdraws proximally into the sheath lumen defined by sheath body 12, the blade 68 of cutting instrument 66 cuts pericardium 52 to create a cut 80 in the pericardium 52. In examples where distal portion 54 is located in a space between the fibrous pericardium and the serous pericardium, the cutting instrument 66 can create the cut 80 in the fibrous pericardium without cutting the serous pericardium. As described herein, a "cut" in the pericardium 52 can refer to a cut in the fibrous pericardium that does not necessarily also pierce the serous pericardium.

Because the blade 68 faces "downwards" towards the distal opening 16 of the sheath lumen, the blade 68 is positioned to cut the pericardium 52 as the catheter body 62 retreats proximally into the distal opening 16 of the sheath lumen. As depicted in FIG. 8, while the cutting instrument 66 is in the actuated position, the catheter body 62 can withdraw proximally within the sheath body 12 until the cutting instrument 66 reaches the distal opening 16 of the sheath lumen defined by sheath body 12. Before the distal portion 64 of catheter body 62 can be fully withdrawn into the sheath body 12, the cutting instrument 66 can be transitioned from the actuated state to the retracted state. But while the cutting instrument 66 is in the actuated state, the cutting instrument 66 can prevent the distal portion 64 of catheter body 62 from fully withdrawing into the sheath body 12.

The catheter mechanism 60 is not limited to making one cut 80 in the pericardium 52 (e.g., the fibrous pericardium) of the patient's heart, as illustrated in FIG. 8. In some examples, the catheter mechanism 60 can make more than one cut in the pericardium 52 (e.g., the fibrous pericardium). For example, the catheter body 62 can make a first cut in the pericardium 52 by withdrawing into the sheath lumen while the cutting instrument 66 is in the actuated state and while the distal tip of sheath body 12 remains in the opening 51 in the pericardium 52. When the first cut is made, the cutting mechanism 66 can transition from the actuated state to the retracted state (e.g., the clinician can control blade actuator 73 to transition the cutting mechanism 66 from the actuated state to the retracted state). Subsequently, the catheter body 62 can be moved to another location to make another cut. The cutting mechanism 66 can transition from the retracted state to the actuated state so that the cutting mechanism 66 can make a second cut in a location separate from the first cut.

To withdraw the catheter body 62 proximally, and into the distal opening 16 of the sheath lumen defined by sheath mechanism 10, the clinician can grip the sheath handle 14 with one hand and grip the catheter handle 70 with another hand. This allows the clinician to guide the catheter mechanism 60 proximally while holding the sheath mechanism 10 in place so that catheter body 62 withdraws proximally to cut the pericardium 52 to create the cut 80.

In some cases, the clinician performs the cut of the pericardium 52 while the portions of the sheath mechanism 10 and the catheter mechanism 60 within the patient's body are under direct visualization by one or more medical imaging systems. For example, a location of the catheter body 62 and the cutting instrument 66 can be visible to the clinician in real time relative to the patient's heart 50 (including pericardium 52). This allows the clinician to determine whether the cutting instrument 66 is positioned properly to make the cut in pericardium 52. The clinician can control catheter mechanism 60 and sheath mechanism 10 to make the cut when the medical imaging indicates that the cutting instrument 66 is positioned properly to make the cut.

Figure 9:
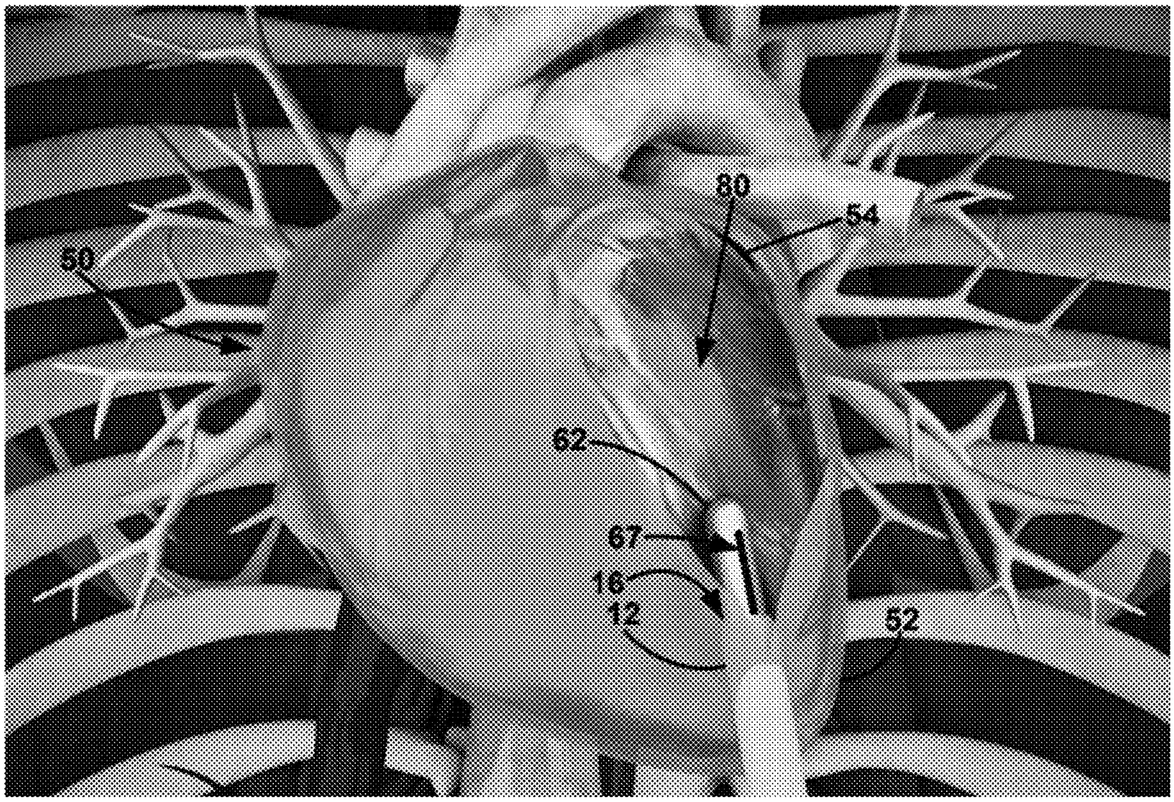
FIG. 9 illustrates the sheath mechanism and the catheter mechanism advanced to the targeted treatment site, the catheter mechanism at least partially retracted to cut the pericardium with the cutting instrument in the retracted position.

Referring now to FIG. 9, the clinician can control the cutting instrument 66 to transition from the actuated state to the retracted state based on the catheter body 62 withdrawing proximally into the sheath lumen to cut the pericardium 52, thus creating the cut 80. In some examples, to transition the cutting instrument 66 from the actuated state to the retracted state, the clinician can first transition the safety mechanism 74 from the engaged position to the disengaged position to allow movement of the mandrel 86 and the transition mechanism 76. The clinician can transition the safety mechanism 74 from the engaged position to the disengaged position by rotating the safety mechanism 74 mounted on the side of the catheter handle 70. Subsequent to transitioning the safety mechanism 74 from the engaged position to the disengaged position by rotating the safety mechanism 74, the clinician can control the transition mechanism 76 to move the mandrel 86 such that the cutting instrument 66 transitions from the actuated position to the retracted position.

In some examples, to transition the cutting instrument 66 from the actuated state to the retracted state, the clinician can rotate the deployment actuator, which in turn moves the mandrel 86 such that the cutting instrument 66 transitions from the actuated position to the retracted position. In some examples, to transition the cutting instrument 66 from the actuated state to the retracted state, the clinician can rotate the rotation actuator, which in turn rotates the mandrel 86 and the deployment mechanism such that the cutting instrument 66 transitions from the actuated position to the retracted position. In any case, to transition from the actuated position to the retracted position, the cutting instrument 66 can rotate into the opening 67 so that cutting instrument 66 is fully within the catheter body 62 and no part of cutting instrument 66 is outside of the catheter body 62, as depicted in FIG. 9.

Figure 10:
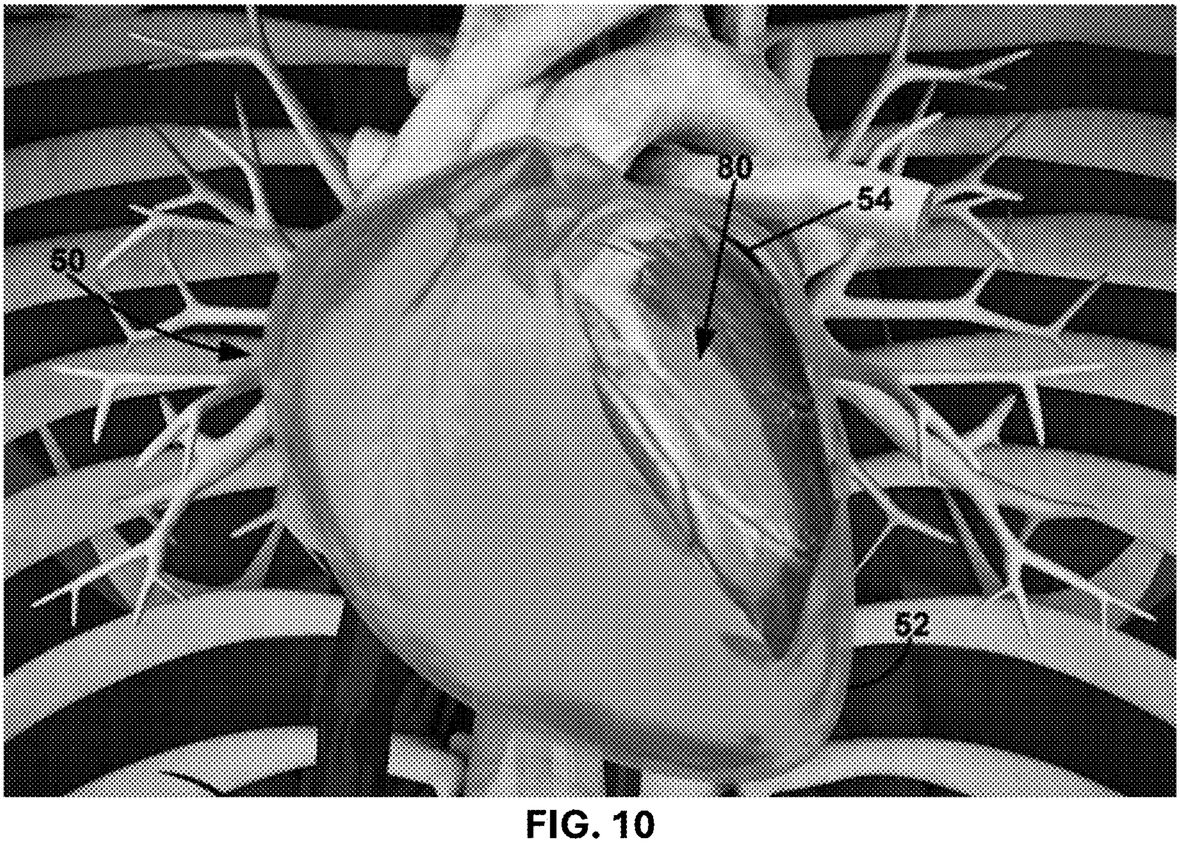
FIG. 10 illustrates the targeted treatment site including a cut in the pericardium created by the catheter mechanism.

Referring now to FIG. 10, the sheath body 12 and the catheter body 62 can be removed from the patient's heart and from the patient's body after the cutting instrument 66 creates the cut 80 in the pericardium 52. Because the clinician can retract the cutting instrument 66 into the opening 67 after making the cut 80 in the pericardium 52, the catheter body 62 and the sheath body 12 can be simultaneously removed from the patient without the cutting instrument 66 causing further damage to tissue of the patient. This is because, when the cutting instrument 66 is retracted, the blade 68 is within the outer housing of catheter body 62 and not in contact with tissue.

In some embodiments, the sheath mechanism 10, the dilator mechanism 30, and the catheter mechanism 60 can perform the process for making the cut 80 in the pericardium 52 that is depicted in FIGS. 2, 3, 5, 6, and 7-10 one time. That is, the procedure involving the sheath mechanism 10, the dilator mechanism 30, and the catheter mechanism 60 can involve a single cut.

In other embodiments, the sheath mechanism 10, the dilator mechanism 30, and the catheter mechanism 60 can make more than one cut in the pericardium 52 according to the process depicted in FIGS. 2, 3, 5, 6, and 7-10. For example, the sheath mechanism 10, the dilator mechanism 30, and the catheter mechanism 60 can make the cut 80 and subsequently make another cut in the pericardium 52 in another location. Additionally, or alternatively, sheath mechanism 10, dilator mechanism 30, and catheter mechanism 60 can make the cut 80 after first making another cut in the pericardium 52.

Figure 11:
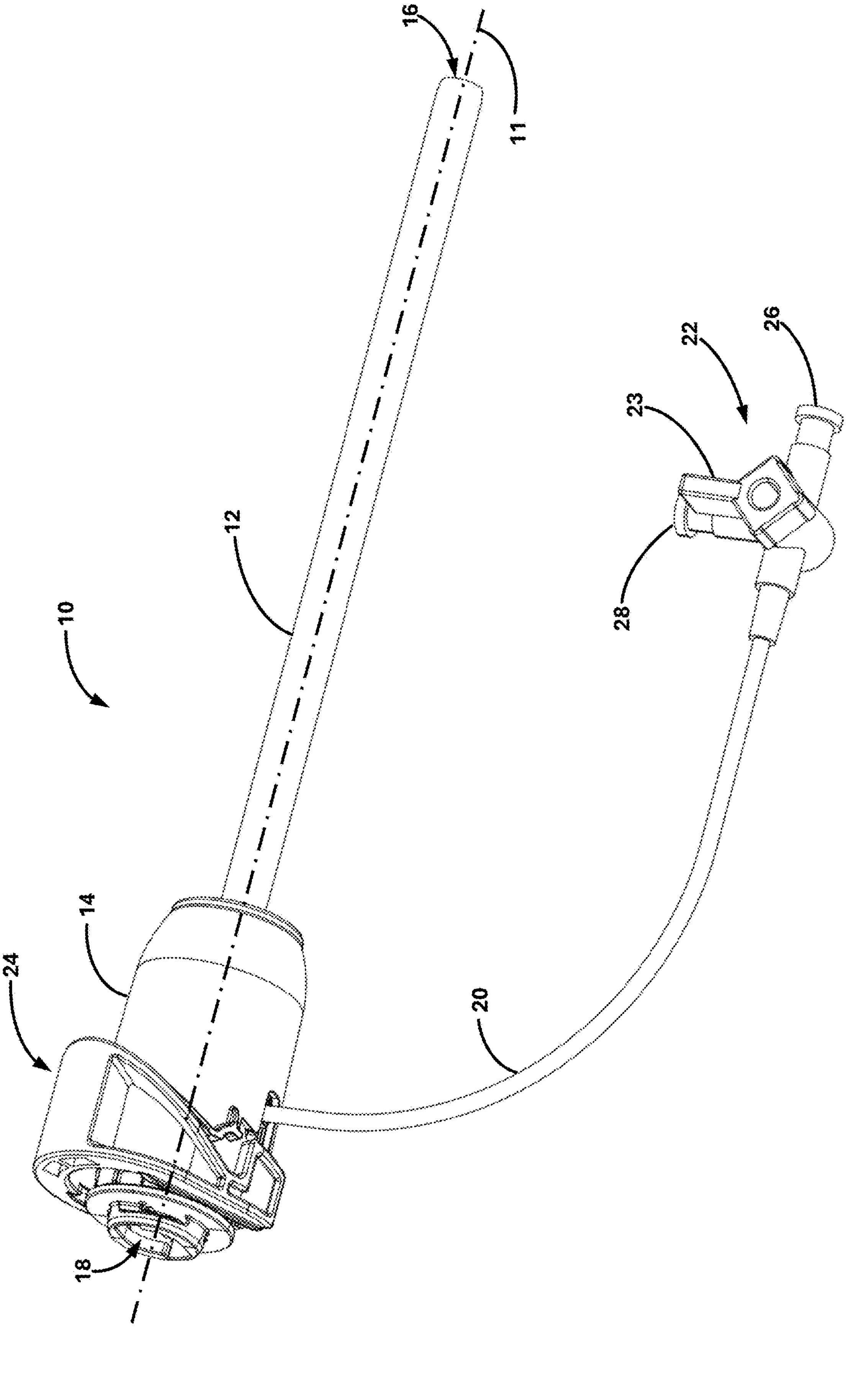
FIG. 11 illustrates a sheath mechanism from a first perspective including a sheath handle and a sheath body.
Figure 18:
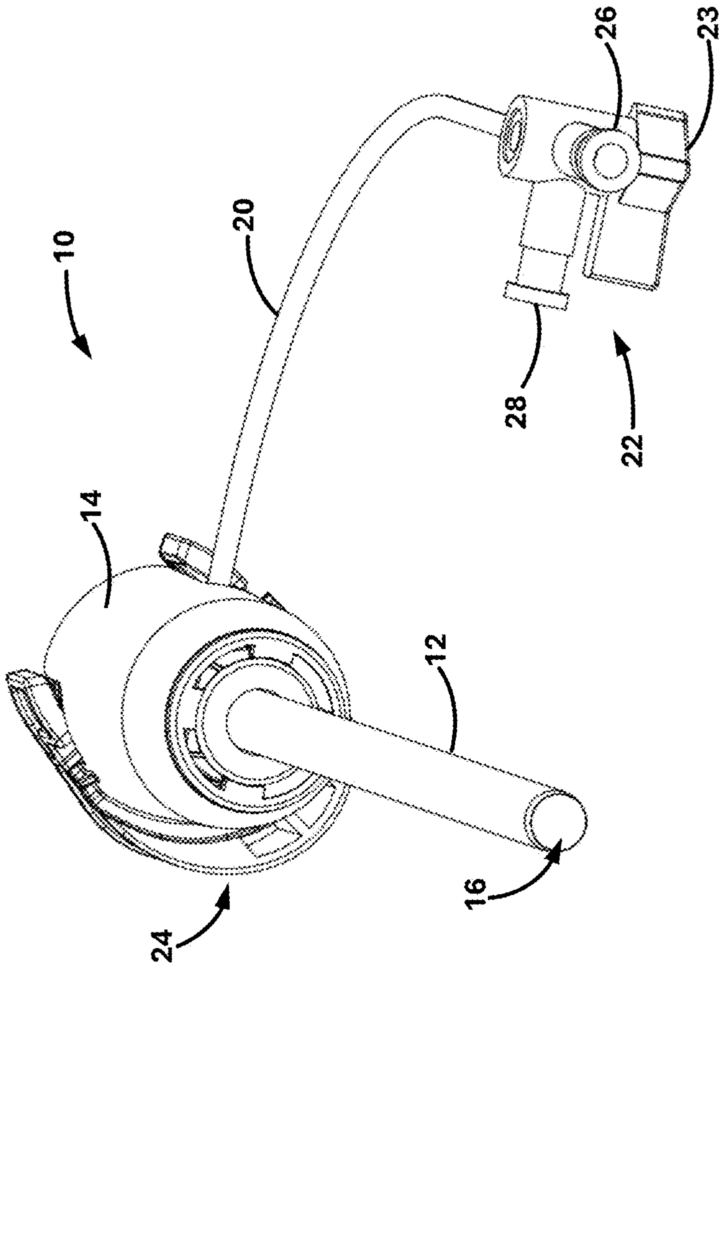
FIG. 18 illustrates the sheath mechanism from a third perspective including a sheath handle and a sheath body.

FIGS. 11 and 18 depict the sheath mechanism 10 without the dilator mechanism 30 or the catheter mechanism 60 inserted into the sheath lumen defined by sheath mechanism 10. The sheath mechanism 10 depicted in FIG. 11 is substantially the same as the sheath mechanism 10 depicted in FIG. 1 and FIG. 4. For example, the sheath mechanism 10 includes sheath body 12 and sheath handle 14 that define a sheath lumen between the distal opening 16 and the proximal opening 18. The sheath lumen, in some examples, is sized to receive the dilator mechanism 30 and the catheter mechanism 60 at different times. For example, the dilator mechanism 30 or the catheter mechanism 60 can be slidably received through the proximal opening 18 to extend through the sheath lumen and beyond the distal opening 16.

As depicted in FIG. 11, flexible tube 20 can be connected to the sheath handle 14. In some examples, the flexible tube 20 can define a fluid lumen that connects to the sheath lumen between the distal opening 16 and the proximal opening 18. This means that fluid can travel through the fluid lumen defined by flexible tube 20 to the sheath lumen defined by the sheath body 12 so that fluid is delivered via the distal opening 16. In some examples, flexible tube 20 is connected to a connector 22 including a valve 23. The connector 22 can include a first Luer connector 26 and a second Luer connector 28. The valve 23 can control whether liquid can flow through one or both of the first Luer connector 26 and the second Luer connector 28. For example, one or both of the first Luer connector 26 and the second Luer connector 28 can connect to a fluid container for holding a liquid contrast agent. In some examples, this liquid contrast agent can flow through connector 22, the flexible tube 20, and the sheath lumen so that sheath mechanism 10 delivers the contrast agent to the patient.

The sheath handle 14 of the sheath mechanism 10 can, in some embodiments, include an air valve 24 that is configured to move along a longitudinal axis 11 of the sheath mechanism 10. For example, the air valve 24 can transition between a first linear position and a second linear position, with the first linear position corresponding to the air valve 24 being open and the linear rotational position corresponding to the air valve 24 being closed. For example, the clinician can push the air valve 24 inwards in a distal direction along sheath handle 14 to transition air valve 24 from being closed to being open. In some embodiments, a default position of air valve 24 is the closed position and force must be applied to push the air valve 24 inwards to open the air valve. In some cases, the air valve 24 includes valve components that automatically seal when an object (e.g., the dilator body 32 or the catheter body 62) inserted into the sheath lumen through the proximal opening 18. When the air valve 24 is closed, the air valve 24 can block air from entering the sheath lumen defined by sheath mechanism 10 and/or block fluid from flowing through the sheath lumen. This means that when the sheath body 12 is inserted into the patient, the air valve 24 can block air from being introduced into subcutaneous tissue areas (e.g., underneath the pericardium 52) when the air valve 24 is closed and/or prevent fluid from escaping from the pericardial space through the sheath lumen when the air valve 24 is closed.

Figure 12:
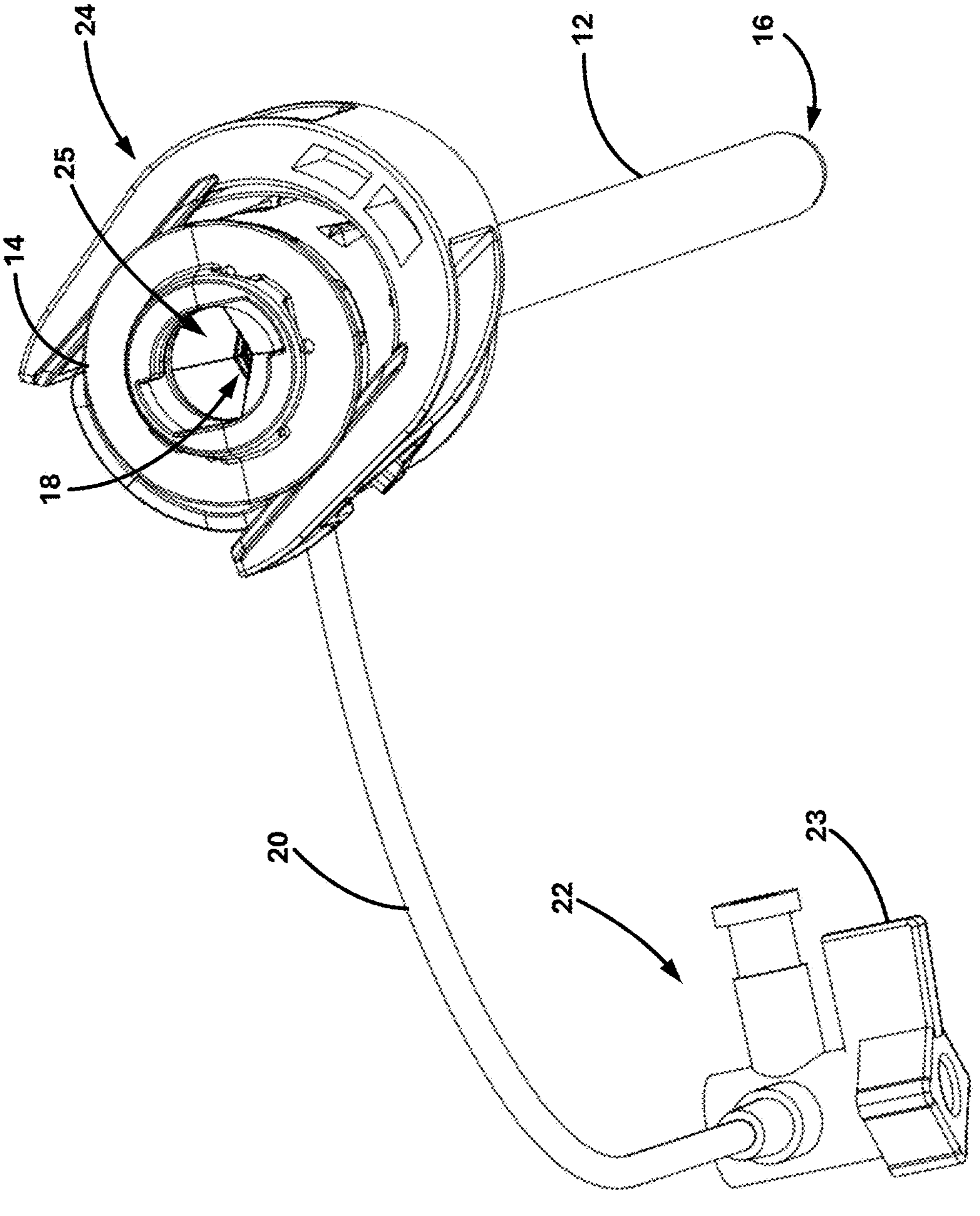
FIG. 12 illustrates a sheath mechanism from a second perspective including a sheath handle and a sheath body.

FIG. 12 depicts the sheath mechanism 10 from another perspective including a view of proximal opening 18 of the sheath lumen. As depicted in FIG. 12, the sheath handle 14 is connected to the sheath body 12 to form a sheath lumen extending between proximal opening 18 and distal opening 16. The flexible tube 20 is connected to a side of the sheath handle 14, and the connector 22 including the valve 23 is connected to flexible tube 20. In some embodiments, the air valve 24 is positioned on the sheath handle 14. In some examples, the air valve 24 can include airlock parts 25 that seal the sheath lumen when the air valve 24 is closed. In some cases, airlock parts 25 can seal the sheath lumen based on a linear position of the air valve 24. In some cases, airlock parts 25 can automatically seal the sheath lumen when there is not an object (e.g., dilator body 32 or catheter body 62) inserted into the sheath lumen through proximal opening 18.

Figure 13:
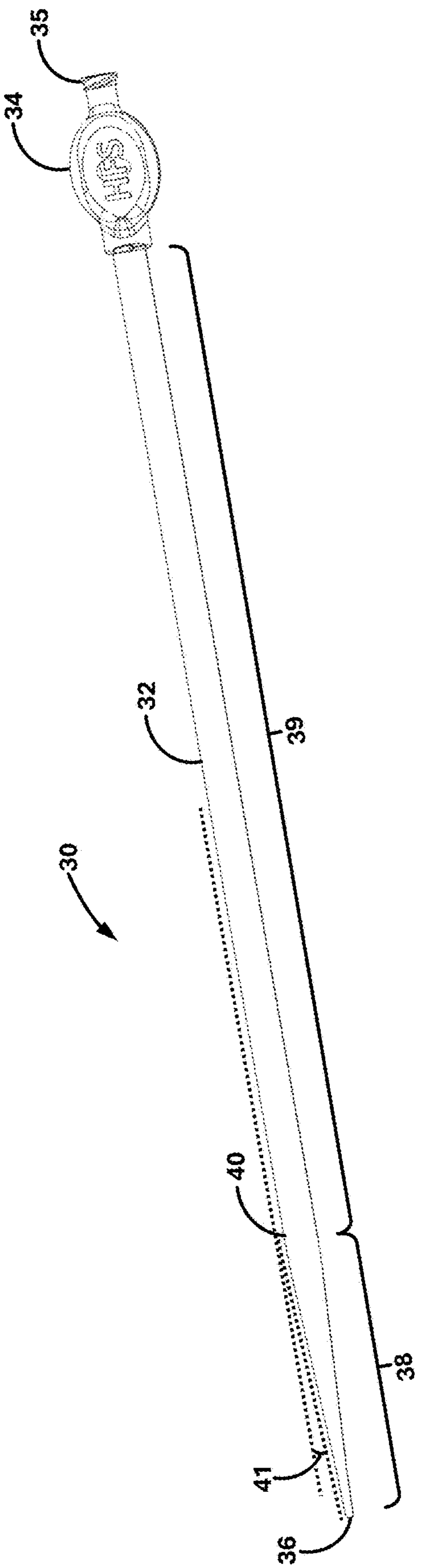
FIG. 13 illustrates a dilator mechanism including a dilator handle and a dilator body.
Figure 20:
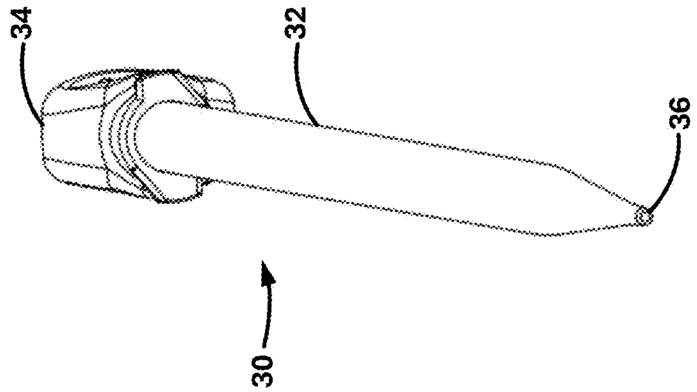
FIGS. 19-20 illustrate the dilator mechanism of FIG. 13 from a different perspectives.
Figure 19:
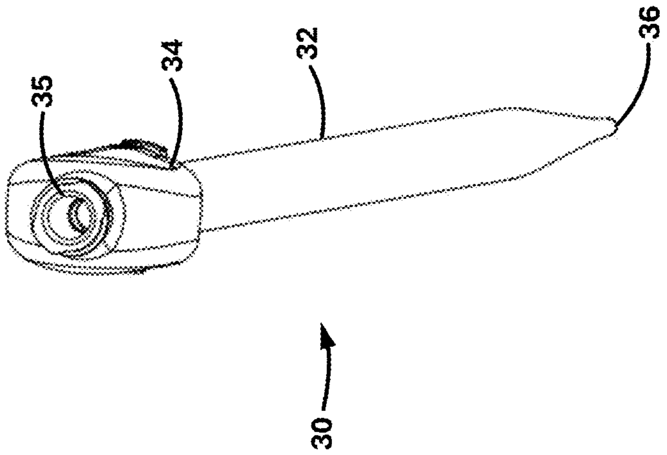

Referring now to FIGS. 13 and 19-20, dilator mechanism 30 can include a dilator body 32 and a dilator handle 34 fixedly attached to the proximal end of dilator body 32. In some examples, the dilator mechanism 30 depicted in FIG. 13 is substantially the same as dilator mechanism 30 depicted in FIG. 1, without being inserted into the sheath lumen defined by sheath mechanism 10. As depicted in FIG. 13, the dilator body 32 includes a distal portion 38 and a proximal portion 39. In some embodiments, the distal portion 38 of the dilator body 32 is tapered so that a diameter of the dilator body 32 decreases moving distally along the dilator body 32 to the distal opening 36.

In some embodiments, dilator body 32 and dilator handle 34 define a dilator lumen that extends through the dilator mechanism 30 between a proximal opening at the port 35 and distal opening 36. In some cases, the dilator lumen is sized to receive the guidewire 56 such that dilator mechanism 30 can advance over the guidewire 56. When the dilator body 32 is received within the sheath lumen of sheath mechanism 10, both of the dilator mechanism 30 and the sheath mechanism 10 can advance over the guidewire 56 simultaneously. In some cases, the dilator mechanism 30 can deliver a liquid contrast agent to a targeted treatment site through the dilator lumen. For example, the port 35 can be connected to a liquid contrast source and liquid contrast can flow through the dilator lumen to be delivered through the distal opening 36.

As depicted in FIG. 13, the distal portion 38 of the dilator body 32 can be tapered. A surface of the distal portion 38 can form an angle 41 with the surface of the proximal portion 39. In some cases, this angle 41 is within a range from 2 degrees to 10 degrees (e.g., 6 degrees). In some examples, the angle between the surface of distal portion 38 and the surface of proximal portion 39 can decrease at least once moving distally along the distal portion 38 of the dilator body 32. For example, the angle 41 between the surface of distal portion 38 and the surface of proximal portion 39 can decrease from a first angle (e.g., 6 degrees) to a second angle (e.g., 3 degrees) smaller than the first angle. These shallow angles can ensure that the distal portion 38 gradually enlarges subcutaneous spaces (e.g., the space between the fibrous pericardium and the serous pericardium) as the dilator body 32 advances into these subcutaneous spaces. In some cases, a diameter of dilator body 32 is substantially constant along the proximal portion 39 of the dilator body 32. This means that the distal portion 38 can dilate (enlarge) a subcutaneous space to the diameter of the proximal portion 39.

Figures 14, 15, 16, 22:
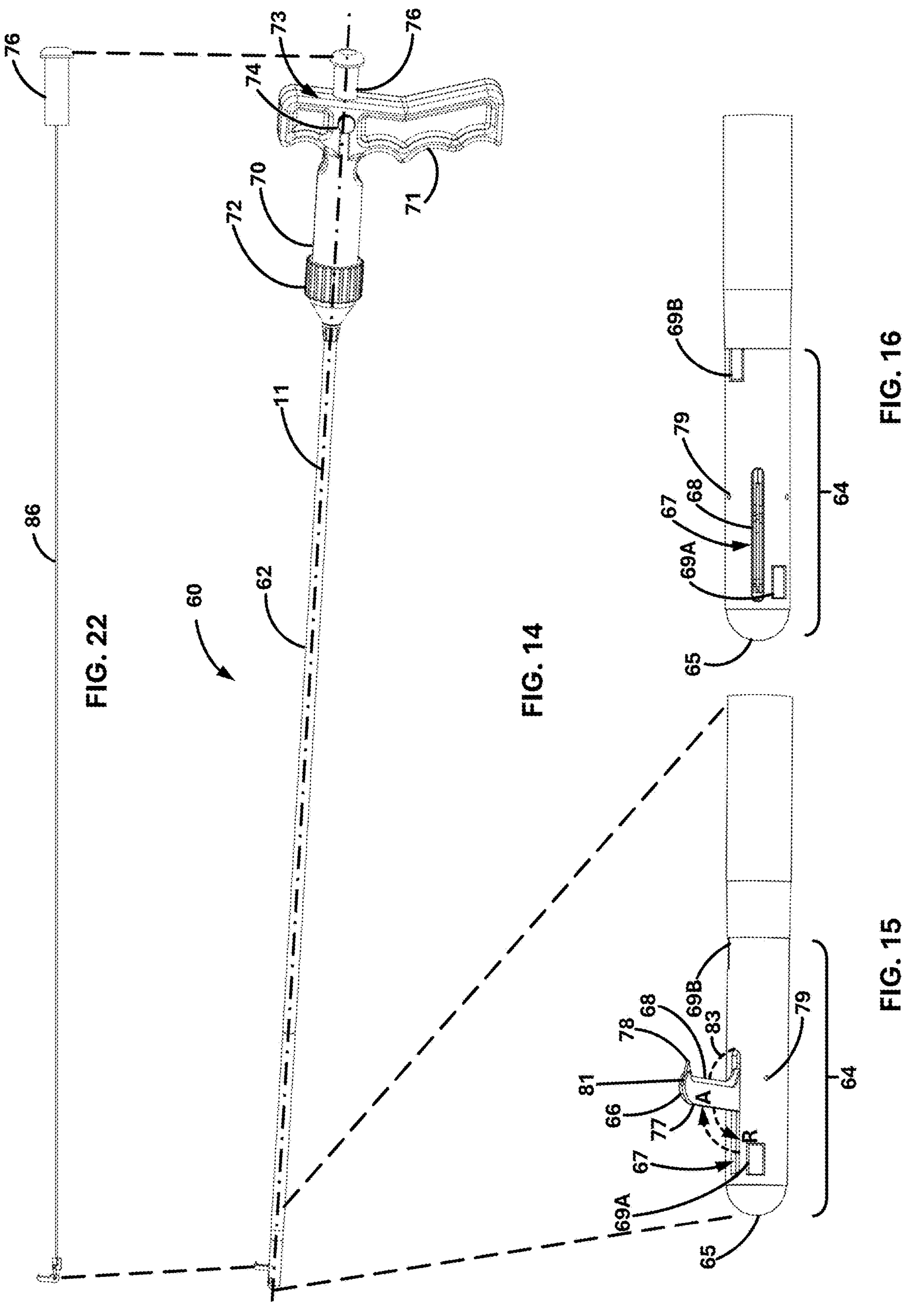
FIG. 14 illustrates a catheter mechanism including a catheter handle and a catheter body.
FIG. 15 illustrates a distal portion of the catheter body while a cutting instrument is in an actuated position.
FIG. 16 illustrates a distal portion of the catheter body while a cutting instrument is in a retracted position.
FIG. 22 illustrates a mandrel for use with the catheter mechanism of FIG. 14.

Referring now to FIGS. 14-16, the catheter mechanism 60 can include a catheter body 62 and a catheter handle 70. The catheter body 62 can, in some embodiments, include a distal portion 64. This distal portion 64 can include a rounded distal tip 65. This distal tip 65 can be rounded so that when catheter body 62 advances through subcutaneous tissue, it does not damage the subcutaneous tissue. A cutting instrument 66 including a blade 68 can be mounted to the distal portion 64 of the catheter body such that the cutting instrument 66 can occupy an actuated position (depicted in FIGS. 14-15) and a retracted position (depicted in FIG. 16). In the actuated position, the cutting instrument 66 can extend outwards from the catheter body 62 such that the blade 68 faces proximally towards the catheter handle 70.

As depicted in FIG. 15, the blade 68 is configured to extend and retract from one side of the cutting instrument 66 so that when cutting instrument 66 is in the actuated position, a sharp edge of the blade 68 faces proximally towards a proximal end of catheter body 62 and away from the distal tip 65 of the catheter body 62. The cutting instrument 66 also includes a blunt edge 77 that is located on the cutting instrument 66, opposite blade 68, so that when the cutting instrument 66 is in the actuated position, the blunt edge 77 faces the distal tip 65 of the catheter body 62. When the cutting instrument 66 is in the actuated position, a proximal movement of catheter body 62 (e.g., a rightwards movement from the perspective of FIG. 15) can cause the blade 68 to cut tissue. In some cases, when the cutting instrument 66 is in the actuated position, a distal movement of the catheter body 62 (e.g., a leftwards movement from the perspective of FIG. 15) can cause less damage to tissue as compared with a proximal movement of the catheter body 62 because the blunt end 77 is not as sharp as the blade 68.

In some examples, the blade 68 can carry radiofrequency (RF) signals. These RF signals can be used to assist in cutting tissue. For example, in some cases, the blade 68 can be connected to a direct current (DC) and/or an alternating current (AC) source via the mandrel 86 passing through the catheter body 62 such that the DC current source delivers an RF signals to blade 68. These RF signals, in some examples, comprise brief pulses of RF energy. The RF signals can cause coagulation of soft tissue that make the tissue easier to cut. This can improve an ability of cutting instrument 66 to cut the pericardium 52 of the heart 50.

The blade 68, in some embodiments, includes a hooked tip 78 that curves inwards from a flat portion of blade 68. This hooked tip 78 can, in some embodiments, pierce tissue of the patient when the cutting instrument 66 transitions from the retracted position to the actuated position. For example, as the cutting instrument 66 rotates out of the opening 67, the hooked tip 78 can move in an arcing motion that pierces the tissue (e.g., the pericardium 52) of the patient. In some cases, this arcing motion can make a puncture into the pericardium 52 so that when the cutting instrument 66 is fully in the actuated position, an end portion of the cutting instrument farthest from the catheter body 62 is outside of the puncture of the pericardium 52 and a body portion of the cutting instrument 66 remains inside of the puncture in the pericardium 52. When the catheter body 62 moves proximally, the blade 68 can enlarge the puncture initially made by the hooked tip 78 in transitioning from the retracted state to the actuated state.

To transition from the retracted position to the actuated position, the cutting instrument 66 can swing outwards from the opening 67 in the catheter body 62 about a hinge 79 in a rotational direction A (e.g., clockwise in FIG. 15). To transition from the actuated position to the retracted position, the cutting instrument 66 can swing into the opening 67 in the catheter body 62 about hinge 79 in a rotational direction R, opposite the rotational direction A (e.g., counterclockwise in FIG. 15). In some examples, the hinge 79 extends through the catheter body 62 and through a rotational axis of the cutting instrument 66 so that the cutting instrument 66 can swing out to extend and swing in to retract about the hinge 79.

When the cutting instrument 66 is in the actuated position, in some embodiments, the cutting instrument 66 extends outward from the catheter body 62 in a direction perpendicular to a longitudinal axis 11 of the catheter body 62 as illustrated in FIG. 15. The cutting instrument 66 is not limited to being perpendicular to the catheter body 62 when in the actuated state. In some examples, cutting instrument 66 (e.g., the sharp edge of the blade 68) forms an angle 83 with the longitudinal axis 11 of the catheter mechanism 60 (e.g., the catheter body 62) when the blade 68 is in the actuated position. The angle 83 can be within a range from 60 degrees to 120 degrees.

In some examples, at least one thermal sensor 95 is located within the distal portion 64 of the catheter body 62 and/or at a predetermined location along the length of the catheter body 62. In some cases, the thermal sensor 95 can include a thermistor, a thermal couple, or another kind of thermal sensor. The thermal sensor 98 can generate an electrical signal indicating a temperature of the space underneath the pericardium 52 (e.g., the space between the fibrous pericardium and the serous pericardium). The clinician can, in some cases, determine whether the distal portion 64 of the catheter body 62 is placed adequately to cut the pericardium 52 based on the electrical signal output by the thermal sensor 95 indicating the temperature.

Figure 24:
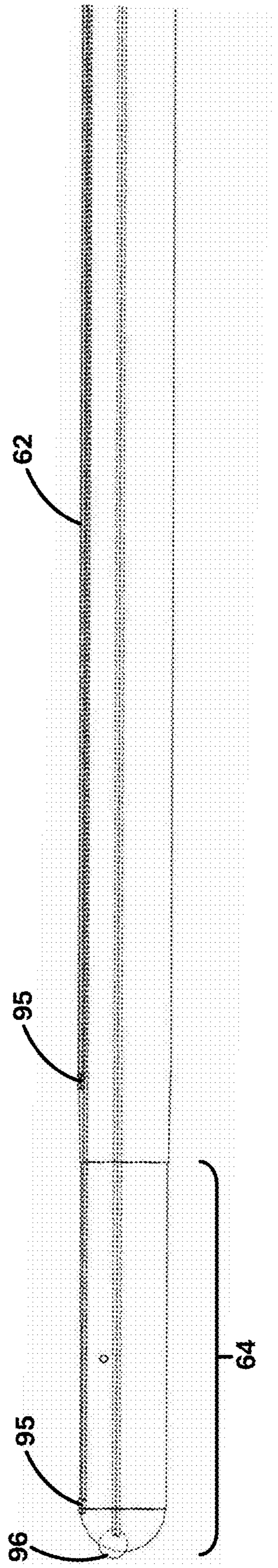
FIG. 24 is an expanded view of a distal end of an embodiment of the catheter mechanism including sensors (e.g.

In some examples, illustrated in FIG. 24, an optical aid 96 is located in the distal portion 64 of the catheter body 62. In some cases, the optical aid 96 may include a camera and/or a light source. The optical aid 96 can be connected to a power source and/or a display screen. The clinician can, in some cases, use the optical aid 96 to observe anatomical positioning and/or verify cut completion.

In some examples, whether the cutting instrument 66 occupies the actuated position (depicted in FIGS. 14-15) or the retracted position (depicted in FIG. 16) can be controllable using the blade actuator 73 on the catheter handle 70. For example, the blade actuator 73 can include a safety mechanism 74 and a transition mechanism 76. When the safety mechanism 74 is disengaged, the transition mechanism 76 can move to transition the cutting instrument 66 between the actuated position and the retracted position. When the safety mechanism 74 is engaged, the cutting instrument 66 can be locked in the actuated position or the retracted position.

In some examples, illustrated in FIG. 22, the blade actuator 73 can include a deployment actuator 75 and the transition mechanism 76. The deployment actuator 75 can be configured to rotate to transition the cutting instrument 66 between the actuated position and the retracted position. The deployment actuator 75 can be self-locking, so that the position of cutting instrument 66 is locked in position once the user stops rotating deployment actuator 75.

Figure 23:
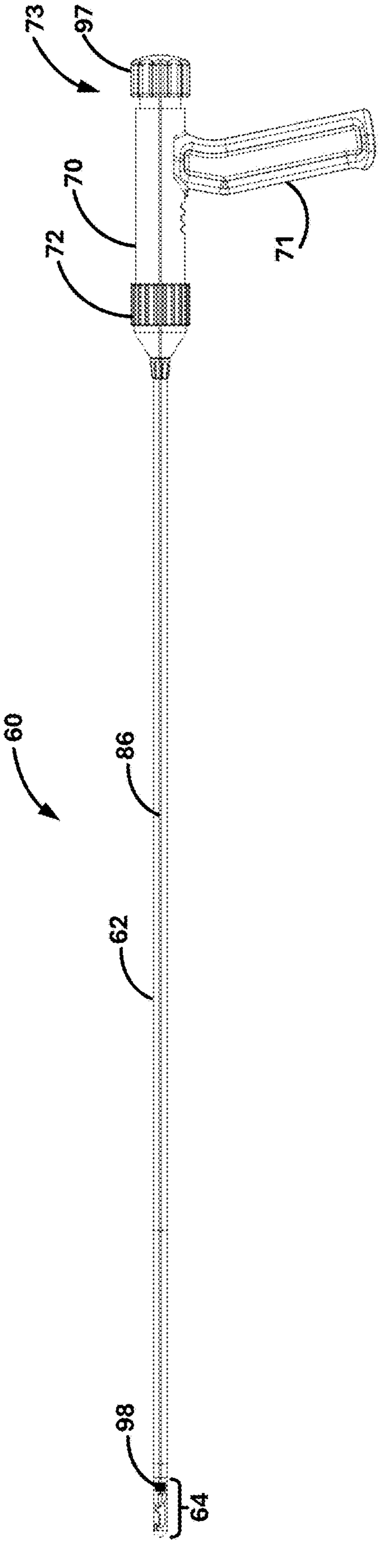
FIG. 23 illustrates an embodiment of the catheter mechanism including a rotation actuator.

In some examples, illustrated in FIG. 23, the blade actuator 73 can include a rotation actuator 97 and a deployment mechanism 98. The rotation actuator 97 can be rotated to transition the cutting instrument 66 between the actuated position and the retracted position. The rotation actuator 97 and/or the deployment mechanism 98 are self-locking, so that the position of cutting instrument 66 is locked in position once the user stops rotating the rotation actuator.

The distal portion 64 of the catheter body 62 can, in some embodiments, include electrodes 69. Each of the electrodes 69 can be mounted to catheter body 62 as part of the outer housing of catheter body 62.

In some examples, each of electrodes 69 can be connected to a respective conductor that extends through the catheter mechanism 60 within the outer housing of the catheter body 62. These conductors can be connected to a pulse generator. The pulse generator can, in some embodiments, generate electrical stimulation for delivery via the electrodes 69 and/or sense electrical stimulation via electrodes 69. In some examples, one of electrodes 69 (e.g., a stimulation electrode 69A) delivers stimulation and one of electrodes 69 (e.g., sense electrode 69B) senses electrical signals.

The electrodes 69 can deliver stimulation and/or sense electrical signals to determine a proximity of one or more nerves (e.g., the phrenic nerve) to the distal portion 64 of the catheter body 62. For example, because the phrenic nerve can be stimulated by electrical stimulation from electrodes 69, the electrodes 69 can sense this nerve activity to determine a proximity of the phrenic nerve to the electrodes 69. The pulse generator connected to electrodes 69, in some examples, can determine the proximity of the phrenic nerve based on the sensed electrical signals.

In an embodiment, the stimulation electrode 69A can be placed at a first location on the outer housing of the catheter mechanism 60 and the sensing electrode 69B can be placed a second location on the outer housing of the catheter mechanism 60, spaced apart from the first location. The blade 68 can be positioned between the first and second locations.

In some examples, the catheter mechanism 60 can define a catheter lumen configured to deliver fluid via an opening 81 on a tip of the cutting instrument 66 while the cutting instrument 66 is in the actuated position. In some examples, this catheter lumen extends from a port on the catheter handle 70 and through the catheter body 62 so that catheter mechanism 60 can deliver the fluid from a liquid source connected to the port on the catheter handle 70 to a targeted treatment site proximate to the opening 81. For example, catheter mechanism 60 can deliver a liquid contrast agent at opening 81. This liquid contrast agent can make the patient's anatomy more visible in medical imaging and/or increase an effectiveness of the stimulation and sensing by electrodes 69 to determine a proximity of the phrenic nerve.

Figure 17:
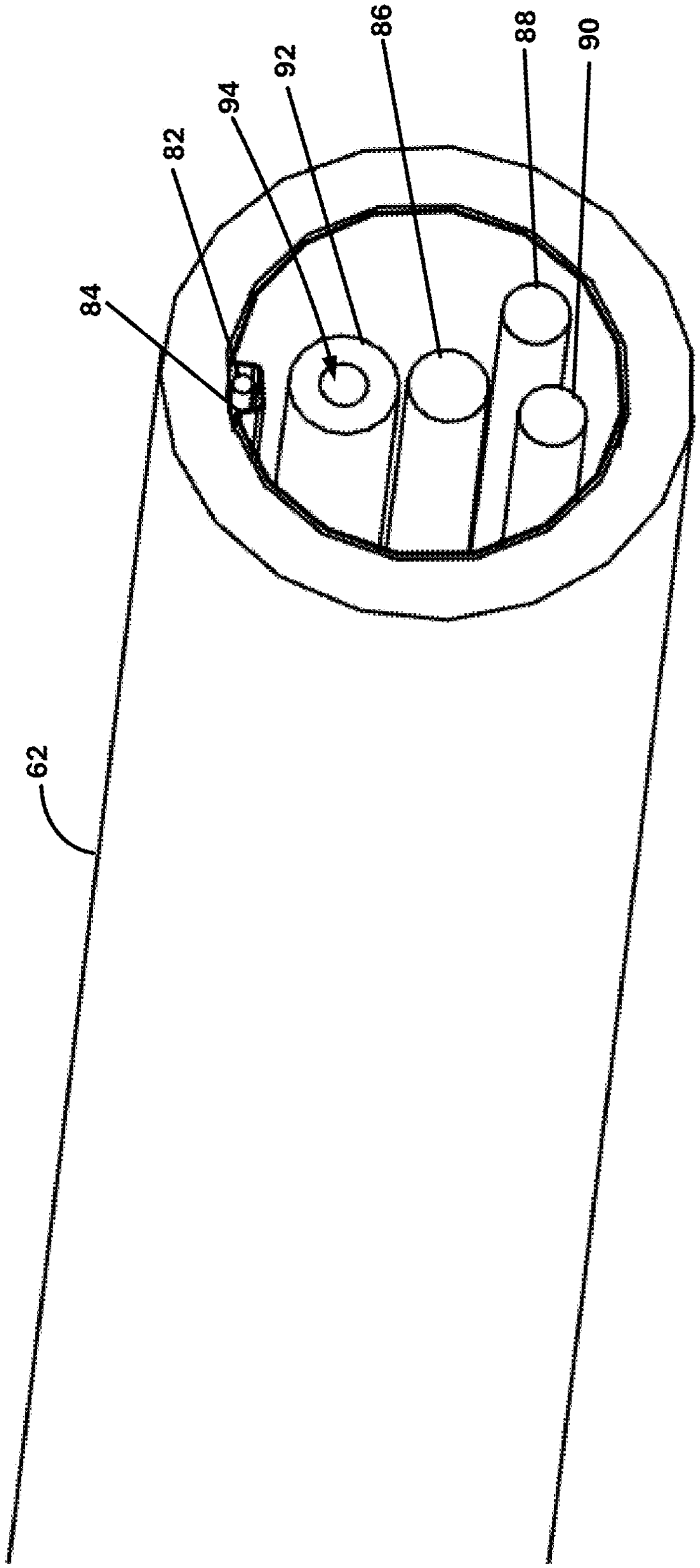
FIG. 17 illustrates a cross-section of the catheter body.

Referring now to FIG. 17, the catheter body 62 includes one or more objects inside of the outer housing of catheter body 62. For example, a pull wire 82 can extend through catheter body 62 to the distal portion 64 within a pull wire enclosure 84. This pull wire 82 can be connected to the deflection actuator 72. Based on a rotation of deflection actuator 72, the pull wire 82 can tighten or relax, causing the catheter body 62 to deflect when the pull wire 82 tightens and relax when the pull wire 82 relaxes.

A mandrel 86, in some examples, can be connected to the cutting instrument 66 and the transition mechanism 76. In some examples, based on the safety mechanism 74 being disengaged, the transition mechanism 76 can move the mandrel 86 within the outer housing of catheter body 62 to transition the cutting instrument 66 between the retracted position and the actuated position. In some examples, the deployment actuator 75 can be rotated to move the transition mechanism 76 and the mandrel 86 within the outer housing of catheter body 62 to transition the cutting instrument 66 between the retracted position and the actuated position.

Conductors 88 and 90 can be connected to the electrodes 69. For example, the conductor 88 can be connected to the stimulation electrode 69A and the conductor 90 can be connected to the sense electrode 69B. Contrast tubing 92 can define a lumen 94 for carrying contrast agent to the opening 81 on the tip of cutting instrument 66. In some embodiments, the space between the objects inside of the outer housing of catheter body 62 is filled with a flexible, solid material.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that further embodiments of the structures and methods illustrated herein may be employed without departing from the principles described herein.

While particular embodiments and applications have been illustrated and described, it is to be understood that the disclosed embodiments are not limited to the precise construction and components disclosed herein. Various modifications, changes, and variations, which will be apparent to those skilled in the art, may be made in the arrangement, operation and details of the method and apparatus disclosed herein without departing from the spirit and scope defined in the appended claims.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

It will be understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.)

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention.

What is claimed is:

1. A catheter system for creating an opening in a pericardium, comprising:

a sheath defining a sheath lumen that includes a distal opening;

a catheter sized to slidably fit within the sheath lumen and configured to extend through an entire length of the sheath lumen with a distal portion of the catheter extending beyond the distal opening of the sheath lumen and into a space underneath the pericardium of a patient;

a blade movably mounted to the distal portion of the catheter to move from a retracted position to an actuated position, the blade including a flat portion having a sharp edge and a hooked tip that curves towards the flat portion;

wherein the blade remains fully within an outer housing of the catheter when the blade is in the retracted position, and wherein the blade is configured to extend outward from the catheter when the blade is in the actuated position to cut the pericardium as the catheter withdraws into the sheath lumen; and a catheter handle attached to a proximal end of the catheter, wherein the catheter handle is located proximal to a proximal opening of the sheath lumen and the catheter extends from the catheter handle through the sheath lumen;

wherein the catheter handle comprises a rotation actuator connected to a mandrel within the outer housing of the catheter, wherein the mandrel is attached to the blade through a deployment mechanism that is configured to, based on movement of the rotation actuator, cause the blade to move from the retracted position to the actuated position.

2. The catheter system of claim 1, wherein the blade extends outward from the catheter and positions the flat portion of the blade perpendicular to a longitudinal axis of the catheter when the blade is in the actuated position.

3. The catheter system of claim 1, wherein the catheter system further comprises:

a stimulation electrode located on the outer housing of the catheter, wherein the stimulation electrode is connected to a pulse generator configured to deliver electrical stimulation to a targeted region proximate a phrenic nerve of the patient, and a sensing electrode located on the outer housing of the catheter, wherein the sensing electrode is connected to sensing circuitry configured to receive a sense signal indicative of a distance between the phrenic nerve and the distal portion of the catheter.

4. The catheter system of claim 3, wherein the stimulation electrode is placed at a first location on the outer housing of the catheter, wherein the sensing electrode is placed at a second location on the outer housing of the catheter, the blade placed between the first location and the second location on the outer housing of the catheter.

5. The catheter system of claim 1, wherein:

the catheter handle comprises a deflection actuator connected to a pull wire within the outer housing of the catheter, and the pull wire is attached to the distal portion of the catheter and, based on the deflection actuator applying tension to the pull wire, the distal portion of the catheter deflects relative to a longitudinal axis of the catheter.

6. The catheter system of claim 5, wherein the deflection actuator comprises a knob rotatably attached on an outer surface of the catheter handle, the deflection actuator applying tension to the pull wire based on rotational movement of the knob to cause the distal portion of the catheter to deflect.

7. The catheter system of claim 6, wherein the knob is rotatably attached on the outer surface of the catheter handle to rotate between a first rotational position corresponding to no deflection of the distal portion of the catheter and a second rotational position corresponding to full deflection of the distal portion of the catheter.

8. The catheter system of claim 1, further comprising:

a guidewire; and a dilator sized to slidably fit within the sheath lumen and extend a distal portion of the dilator beyond the distal opening of the sheath lumen when the catheter is outside of the sheath lumen;

wherein the dilator is further configured to enlarge the space underneath the pericardium of the patient for subsequent insertion of the catheter when the dilator and the sheath simultaneously advance into the patient along the guidewire.

9. The catheter system of claim 8, wherein the distal portion of the dilator is tapered and a diameter of the dilator decreases moving distally along the distal portion of the dilator.

10. The catheter system of claim 9, wherein an outer surface of the distal portion of the dilator forms an angle with an outer surface of a proximal portion of the dilator.

11. The catheter system of claim 10, wherein the angle is within a range from two degrees to eight degrees.

12. The catheter system of claim 9, further comprising a dilator handle attached to a proximal end of the dilator, wherein a width of the dilator handle is greater than a diameter of a proximal opening of the sheath lumen to prevent the dilator handle from entering the sheath lumen.

13. The catheter system of claim 12, wherein the dilator handle comprises a fluid input port in fluid communication with a dilator lumen extending through the dilator, from the input port to a distal opening of the dilator, and wherein the input port is configured to connect to a liquid contrast source to deliver a liquid contrast agent through the dilator lumen.

14. The catheter system of claim 1, wherein the catheter defines a catheter lumen sized to convey a liquid contrast agent therethrough.

15. The catheter system of claim 1, further comprising a sheath handle, wherein a first end of the sheath handle is attached to a proximal end of the sheath and a second, opposing end the sheath handle is attached to a tube for conveying liquid contrast agent to the sheath lumen.

16. The catheter system of claim 15, further comprising a connector including a valve in fluid communication with the sheath handle via the tube and configured to transition between a closed position and an open position, wherein the valve prevents gases and liquids from flowing through the connector and the sheath lumen when the valve is in the closed position and permits gases and liquids to flow through the connector and the sheath lumen when the valve is in the open position.

17. The catheter system of claim 1, wherein the blade is configured to make one or more cuts in the pericardium as the catheter withdraws into the sheath lumen.

18. The catheter system of claim 17, wherein the blade is configured to make one cut in the pericardium as the catheter withdraws into the sheath lumen.

19. The catheter system of claim 17, wherein the blade is configured to make a first cut in a first location of the pericardium as the catheter withdraws into the sheath lumen, and to make a second cut in a second location of the pericardium as the catheter withdraws into the sheath lumen.

20. The catheter system of claim 1, further comprising a thermal sensor located on the distal portion of the catheter, the thermal sensor configured to generate an electrical signal indicating a temperature of the space underneath the pericardium of the patient.

21. The catheter system of claim 1, further comprising an optical aid located in the distal portion of the catheter, the optical aid configured to provide real time video footage.

22. The catheter system of claim 1, wherein the blade is configured to carry radiofrequency (RF) signals for cutting tissue.

23. The catheter system of claim 1, wherein the sharp edge proximally faces a catheter body when the blade is in the actuated position and the blade further comprises a blunt edge opposite the sharp edge, that distally faces the catheter body when the blade is in the actuated position.

24. A catheter system for creating an opening in a pericardium, comprising:

a sheath defining a sheath lumen that includes a distal opening;

a dilator sized to slidably fit within the sheath lumen and extend a distal portion of the dilator beyond the distal opening of the sheath lumen, wherein the dilator is configured to enlarge a space underneath the pericardium of a patient when the dilator and the sheath simultaneously advance into the patient along a guidewire;

a catheter sized to slidably fit within the sheath lumen after the dilator is removed from the sheath lumen, wherein a distal portion of the catheter is configured to extend beyond the distal opening of the sheath lumen and into the space underneath the pericardium of the patient;

a blade mounted on the distal portion of the catheter and including a flat portion and a hooked tip that curves towards the flat portion, wherein the blade is configured for cutting the pericardium as the catheter withdraws into the sheath lumen; and a catheter handle attached to a proximal end of the catheter, wherein the catheter handle is located proximal to a proximal opening of the sheath lumen and the catheter extends from the catheter handle through the sheath lumen;

wherein the catheter handle comprises a rotation actuator connected to a mandrel within an outer housing of the catheter, wherein the mandrel is attached to the blade through a deployment mechanism that is configured to, based on movement of the rotation actuator, cause the blade to move from a retracted position to an actuated position for cutting the pericardium.

25. A catheter system for creating an opening in a pericardium, comprising:

a sheath defining a sheath lumen that includes a distal opening;

a catheter sized to slidably fit within the sheath lumen and configured to extend through an entire length of the sheath lumen with a distal portion of the catheter extending beyond the distal opening of the sheath lumen and into a space underneath the pericardium of a patient;

a blade movably mounted to the distal portion of the catheter to move from a retracted position to an actuated position, the blade including a flat portion having a sharp edge and a hooked tip that curves towards the flat portion;

wherein the blade remains fully within an outer housing of the catheter when the blade is in the retracted position, and wherein the blade is configured to extend outward from the catheter when the blade is in the actuated position to cut the pericardium as the catheter withdraws into the sheath lumen; and a catheter handle attached to a proximal end of the catheter, wherein the catheter handle is located proximal to a proximal opening of the sheath lumen and the catheter extends from the catheter handle through the sheath lumen;

wherein the catheter handle comprises a blade actuator connected to a mandrel within the outer housing of the catheter, wherein the mandrel is attached to the blade and, based on movement of the blade actuator, the mandrel causes the blade to move from the retracted position to the actuated position; and wherein the blade actuator comprises:

a safety mechanism rotatably attached on an outer surface of the catheter handle and configured to rotate between an engaged position and a disengaged position; and a transition mechanism slidably attached to the catheter handle, wherein the transition mechanism is attached to the mandrel and configured to move the mandrel within the outer housing of the catheter when the safety mechanism is in the disengaged position to cause the blade to move from the retracted position to the actuated position.

26. A catheter system for creating an opening in a pericardium, comprising:

a sheath defining a sheath lumen that includes a distal opening;

a catheter sized to slidably fit within the sheath lumen and configured to extend through an entire length of the sheath lumen with a distal portion of the catheter extending beyond the distal opening of the sheath lumen and into a space underneath the pericardium of a patient;

a blade movably mounted to the distal portion of the catheter to move from a retracted position to an actuated position, the blade including a flat portion having a sharp edge and a hooked tip that curves towards the flat portion;

wherein the blade remains fully within an outer housing of the catheter when the blade is in the retracted position, and wherein the blade is configured to extend outward from the catheter when the blade is in the actuated position to cut the pericardium as the catheter withdraws into the sheath lumen; and a catheter handle attached to a proximal end of the catheter, wherein the catheter handle is located proximal to a proximal opening of the sheath lumen and the catheter extends from the catheter handle through the sheath lumen;

wherein the catheter handle comprises a blade actuator connected to a mandrel within the outer housing of the catheter, wherein the mandrel is attached to the blade and, based on movement of the blade actuator, the mandrel causes the blade to move from the retracted position to the actuated position; and wherein the blade actuator comprises:

a transition mechanism slidably attached to the catheter handle, wherein the transition mechanism is attached to the mandrel and configured to move the mandrel within the outer housing of the catheter to cause the blade to move from the retracted position to the actuated position; and a self-locking deployment actuator rotatably attached to catheter handle to control movement of the transition mechanism.

* * * * *